(12) United States Patent
Takahashi

(10) Patent No.: US 12,394,170 B2
(45) Date of Patent: Aug. 19, 2025

(54) CELL IMAGE ANALYSIS METHOD AND CELL IMAGE ANALYZER

(71) Applicant: SHIMADZU CORPORATION, Kyoto (JP)

(72) Inventor: Wataru Takahashi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 17/578,179

(22) Filed: Jan. 18, 2022

(65) Prior Publication Data

US 2022/0148282 A1    May 12, 2022

Related U.S. Application Data

(63) Continuation of application No. PCT/JP2019/028268, filed on Jul. 18, 2019.

(51) Int. Cl.
*G06V 10/22* (2022.01)
*C12M 1/34* (2006.01)
*C12Q 1/04* (2006.01)
*G06V 10/46* (2022.01)
*G06V 10/70* (2022.01)
*G06V 10/774* (2022.01)
*G06V 20/69* (2022.01)

(52) U.S. Cl.
CPC ............ *G06V 10/235* (2022.01); *C12M 1/34* (2013.01); *C12Q 1/04* (2013.01); *G06V 10/46* (2022.01); *G06V 10/70* (2022.01); *G06V 10/774* (2022.01); *G06V 20/69* (2022.01); *G06V 20/695* (2022.01)

(58) Field of Classification Search
None
See application file for complete search history.

(56) References Cited

U.S. PATENT DOCUMENTS 8,902,306 B2    12/2014  Mimura et al.
2015/0087240 A1*  3/2015  Loewke ................. G06T 7/143
                                                          455/67.11
2016/0370569 A1* 12/2016  Matsumoto ........ G01N 15/1475
(Continued)

FOREIGN PATENT DOCUMENTS

JP    2011-229409 A    11/2011
JP    4968595 B2        4/2012
(Continued)

OTHER PUBLICATIONS

Written Opinion by the International Search Authority for PCT application PCT/JP2019/028268 dated Jan. 10, 2019, submitted with a machine translation.
(Continued)

*Primary Examiner* — Ming Y Hon
*Assistant Examiner* — Dominique James
(74) *Attorney, Agent, or Firm* — Muir Patent Law, PLLC

(57) ABSTRACT

A cell image analysis method includes converting a first image into a label image by performing a segmentation process to identify a region of a cell that has already started differentiation and a region of an undifferentiated cell in the first image, acquiring a shape feature amount from the label image, and determining whether or not a cell colony includes a colony region that is a candidate for a search target based on the shape feature amount and a determination criterion.

9 Claims, 15 Drawing Sheets

(56) References Cited

U.S. PATENT DOCUMENTS

| | | | |
|---|---|---|---|
| 2019/0287244 A1* | 9/2019 | Wakui | C12M 41/36 |
| 2020/0135328 A1* | 4/2020 | Yamada | G16H 40/20 |
| 2020/0192059 A1 | 6/2020 | Wakui | |
| 2020/0342597 A1* | 10/2020 | Chukka | G06V 20/698 |
| 2021/0117729 A1* | 4/2021 | Bharti | G01N 15/1429 |
| 2021/0133963 A1* | 5/2021 | Takahashi | G06T 7/62 |
| 2021/0272288 A1* | 9/2021 | Takahashi | G06N 3/045 |

FOREIGN PATENT DOCUMENTS

| | | |
|---|---|---|
| JP | 5181385 B2 | 1/2013 |
| WO | 2017/056600 A1 | 4/2017 |
| WO | 2018/105432 A1 | 6/2018 |
| WO | 2019/044424 A1 | 7/2019 |

OTHER PUBLICATIONS

Takahashi et al., "Development segmentation technique for recognition of undifferentiated aberrant colonies of iPS Cells Using deep learning", 2018, Medical Science Digest, vol. 44, No. 9, p. 483-486.

Cell Culture Analysis Device CS-1, online search on Feb. 14, 2017, URL: https://www.an.shimadzu.co.jp/bio/cell/cs1/index.htm.

Long et al., "Fully Convolutional Networks for Semantic Segmentation", The IEEE Conference on Computer Vision and Pattern Recognition, 2015, pp. 3431-3440 URL:https://people.eecs.berkeley.edu/~jonlong/long_shelhamer_fcn.pdf.

Ronneberger et al., "U-Net: Convolutional Networks for Biomedical Image Segmentation", Computer Science Department and BIOSS Centre for Biological Signalling Studies, University of Freiburg, Germany URL:https://arxiv.org/abs/1505.04597, downloaded May 13, 2019.

Notice of Reasons for Refusal dated Nov. 1, 2022 for corresponding Japanese Patent Application No. JP 2021-532644.

First Office Action dated Dec. 28, 2023 issued in relation to the corresponding Chinese Patent Application No. 201980098569.7 together with a machine English translation thereof.

Second Office Action dated Jul. 9, 2024 for corresponding Chinese Patent Application No. 201980098569.7.

* cited by examiner

FIG.7

| SHAPE FEATURE AMOUNTS | | |
|---|---|---|
| 25A → COLONY FEATURE AMOUNTS | AREA OF COLONY | 25 |
| | CONTOUR LENGTH OF COLONY | 25 |
| | DEGREE OF CIRCULARITY OF COLONY | 25 |
| | ASPECT RATIO OF COLONY | 25 |
| 25B → UNDIFFERENTIATED REGION FEATURE AMOUNTS | AREA OF UNDIFFERENTIATED REGION | 25 |
| | CONTOUR LENGTH OF UNDIFFERENTIATED REGION | 25 |
| | DEGREE OF CIRCULARITY OF UNDIFFERENTIATED REGION | 25 |
| | ASPECT RATIO OF UNDIFFERENTIATED REGION | 25 |
| 25C → DEVIANT REGION FEATURE AMOUNT | AREA OF DEVIANT REGION | 25 |
| | UNDIFFERENTIATED AREA RATIO | 25 |

FIG.8

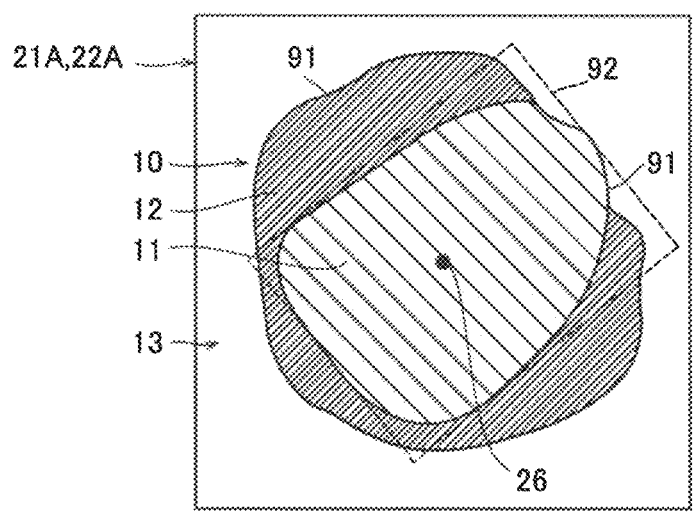

FIG. 13   CELL IMAGE ANALYSIS AND PICKING PROCESS

EXAMPLES OF DETERMINATION CRITERIA FOR PICKING TARGET

- DETERMINATION RESULT (CERTAINTY) IS LARGER THAN THRESHOLD
- RANK OF DETERMINATION RESULT (CERTAINTY) IS HIGHER THAN THRESHOLD
- INPUT OF PICKING TARGET IS RECEIVED FROM USER

CELL IMAGE ANALYSIS METHOD AND CELL IMAGE ANALYZER

CROSS-REFERENCE TO RELATED APPLICATION

This application is a continuation of PCT application PCT/JP2019/028268, filed on Jul. 18, 2019.

BACKGROUND OF THE INVENTION

Field of the Invention

The present invention relates to a cell image analysis method and a cell image analyzer.

Description of the Background Art

Conventionally, it is known to culture pluripotent cells such as induced pluripotent stem cells (iPS cells).

In cell culture, cells being cultured are extracted from a culture vessel and transferred to another culture vessel such that passaging is performed to obtain a next-generation cell line. This extraction of cells is called picking. There are cells unsuitable for passaging such as cells that have already started differentiation (cells that have lost pluripotency) in the culture vessel, and thus cells suitable for passaging are selected by an operator (user) at the time of passaging.

Specifically, the operator (user) searches for cells suitable for passaging from the culture vessel by checking cell colonies in the culture vessel one by one with a microscope. Then, the operator (user) marks a position at which the cells suitable for passaging are located, and suctions a cell colony at the marked position with a pipetter, for example. Furthermore, at the initial stage of culture, cells that have already started differentiation (cells that have lost pluripotency), dead cells, etc. are extracted and removed from the culture vessel. Similarly to the passaging, such a removal operation is also performed by searching for a removal target using a microscope and picking the found removal target.

Such a cell search operation and a picking operation are delicate and burdensome to the user, and thus a device configured to automate a portion of the operations has been proposed (see Non-Patent Document 1, for example). Non-Patent Document 1 discloses a device configured to automatically perform a cell picking operation with a pipetter by operating a controller after a microscope image of cells in a culture vessel is captured and a user determines a picking target from the image.

Even with the device disclosed in Non-Patent Document 1, it is necessary for the user to perform a cell search operation by himself/herself, and thus it is desired to reduce the workload on the user for the cell search operation.

However, cells to be picked differ depending on the purpose of the cell culture carried out by the user and the type of cells to be cultured, for example. Therefore, it is necessary for the user to independently determine which cell region is suitable for the picking target from among a large number of cell regions observed from the microscope image. Consequently, conventionally, when pluripotent cells are cultured, it has been difficult to reduce the load on the user associated with an operation to search for a picking target.

SUMMARY OF THE INVENTION

The present invention is intended to solve the above problem. The present invention aims to provide a cell image analysis method and a cell image analyzer capable of effectively reducing the load on a user associated with an operation to search for cells to be picked in cell culture.

In order to attain the aforementioned object, a cell image analysis method according to a first aspect of the present invention includes acquiring a first image of a cell colony including a cell having differentiation potential, converting the first image into a label image by performing a segmentation process to identify a colony region of a cell that has already started differentiation and a colony region of an undifferentiated cell in the cell colony in the first image, acquiring a shape feature amount of the cell colony from the label image, receiving an input regarding a colony region of a search target from a user using a computer, setting a determination criterion for the shape feature amount based on the user's input, and determining whether or not the cell colony includes a colony region that is a candidate for the search target based on the shape feature amount and the determination criterion.

A cell image analyzer according to a second aspect of the present invention includes a storage configured to allow a microscope image of a cell colony including a cell having differentiation potential to be input thereto, a segmentation processing unit configured to convert the microscope image into a label image by performing a segmentation process to identify a colony region of a cell that has already started differentiation and a colony region of an undifferentiated cell in the cell colony in the microscope image, an input configured to receive an input regarding a colony region of a search target, and a determination processing unit configured to determine whether or not the cell colony included in the microscope image includes the colony region that is a candidate for the search target. The determination processing unit is configured to acquire a shape feature amount of the cell colony from the label image and determine a colony region based on the shape feature amount and a determination criterion for the shape feature amount set based on a user's input.

A cell image analysis method according to a third aspect of the present invention includes creating a machine-trained model for determination, acquiring a first image of a cell colony including a cell having differentiation potential, converting the first image into a label image by performing a segmentation process to identify a colony region of a cell that has already started differentiation and a colony region of an undifferentiated cell in the cell colony in the first image, and determining whether or not the cell colony includes the colony region that is a candidate for a search target by inputting the label image of the first image to the trained model. The creating of the trained model includes receiving an input of selection information as to whether or not the cell colony in a second image acquired in advance includes a desired colony region, and creating the trained model by machine learning using a label image obtained by segmenting the second image as input data and the selection information as teaching data.

Effect of the Invention

According to the first to third aspects of the present invention, as described above, among colony regions including one (ones) of a cell that has started differentiation and another (others) of an undifferentiated cell, a colony region that may be a picking target in accordance with the purpose of culture or the like can be identified from the image by the segmentation process. Furthermore, according to the first and second aspects, the determination result as to whether or not the cell colony in the image includes the colony region that is the candidate for the search target can be obtained based on the shape feature amount and the determination criterion for the shape feature amount set based on the user's input. According to the third aspect, the determination result as to whether or not the cell colony in the image includes the colony region that is the candidate for the search target can be obtained by the trained model machine-trained using the selection information as to whether or not the cell colony includes the desired colony region. Consequently, according to the first to third aspects of the present invention, the cell colony including the colony region that is likely to be determined by the user as the picking target can be determined and shown to the user, and thus it is no longer necessary for the user to observe and determine a large number of cell regions one by one. Thus, the load on the user associated with the search operation for cells to be picked in cell culture can be effectively reduced.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 7 is a diagram showing examples of shape feature amounts.

FIG. 8 is a schematic view of a label image for illustrating the shape feature amounts.

FIG. 13 is a flowchart illustrating a cell image analysis process and a picking process.

DESCRIPTION OF THE PREFERRED EMBODIMENTS

An embodiment embodying the present invention is hereinafter described on the basis of the drawings.

A cell image analysis method and a cell image analyzer 100 according to this embodiment are now described with reference to FIGS. 1 to 14.

Cell Image Analysis Method

Figure 1:
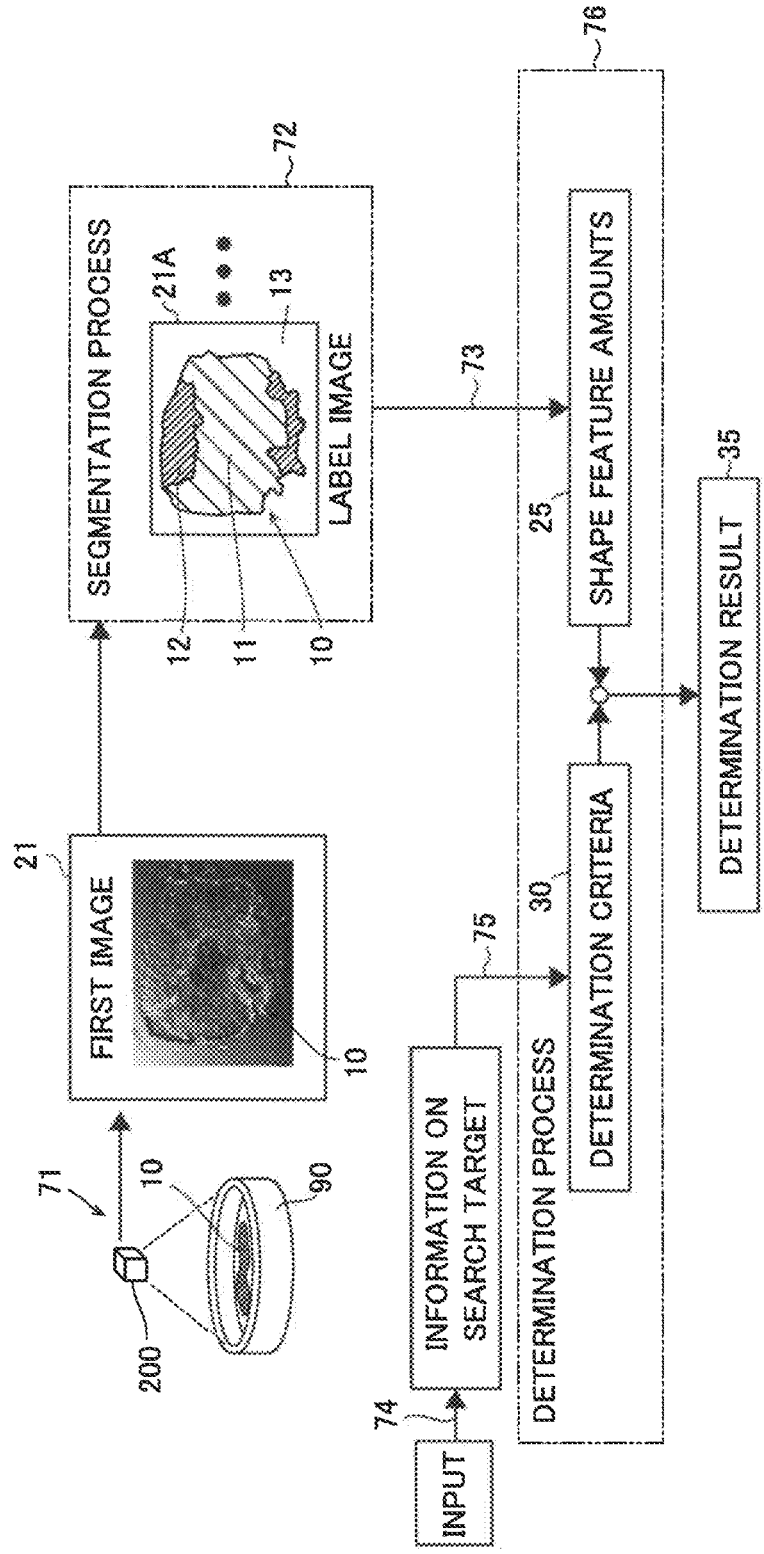
FIG. 1 is a diagram showing the outline of a cell image analysis method according to an embodiment.

In the cell image analysis method shown in FIG. 1, in a cell picking operation in cell culture, a microscope image of a cell colony 10 is acquired, and whether or not the cell colony 10 appearing in the microscope image includes a colony region that is a candidate for a search target is determined.

The cell colony 10 refers to a cell mass (an aggregate of a large number of cells) derived from a single cell. The colony region refers to a region of the cell colony including specific cells.

The cell picking refers to extracting a cell or a cell mass to be picked from a cell culture vessel 90. The cell picking is performed by suctioning a picking target using an instrument such as a pipetter.

The cell to be picked in this embodiment is a cell having differentiation potential. The cell having differentiation potential is an iPS cell or an ES cell (embryonic stem cell), for example. These cells have pluripotent differentiation (differentiation potential) to differentiate into cells of various tissues and organs. In such cell culture, "undifferentiated cells", which maintain pluripotency, and "undifferentiated deviant cells", which have deviated from the undifferentiated state and have already started to differentiate, are generated. Therefore, a colony region of the undifferentiated cells and a colony region of the undifferentiated deviant cells are formed in the cell colony. The cell colony may include only the colony region of the undifferentiated cells or the colony region of the undifferentiated deviant cells, or may include the colony region of the undifferentiated cells and the colony region of the undifferentiated deviant cells.

In order to grow the undifferentiated cells that maintain pluripotency, an operation called passaging in which undifferentiated cells are picked and transferred to another culture vessel to obtain a next-generation cell line or an operation to pick undifferentiated deviant cells and remove them from the culture vessel 90 is performed.

For example, it is not that cells used for passaging can be any undifferentiated cells. When performing picking, a user searches for a colony region of undifferentiated cells according to the purpose of the user performing a culture operation and selects the colony region of undifferentiated cells as a picking target.

In the cell image analysis method according to this embodiment, a colony region 11 of undifferentiated cells is distinguished from a colony region 12 of undifferentiated deviant cells when cells having such differentiation potential are cultured. Then, in the cell image analysis method, the cell colony 10 including a colony region that is a candidate for a search target for picking is determined according to the purpose of the user performing the culture operation such that an operation to search for the cell colony 10 to be picked is supported. The colony region 12 of undifferentiated deviant cells is an example of a "colony region of cells that have already started differentiation" in the claims.

Figure 2:
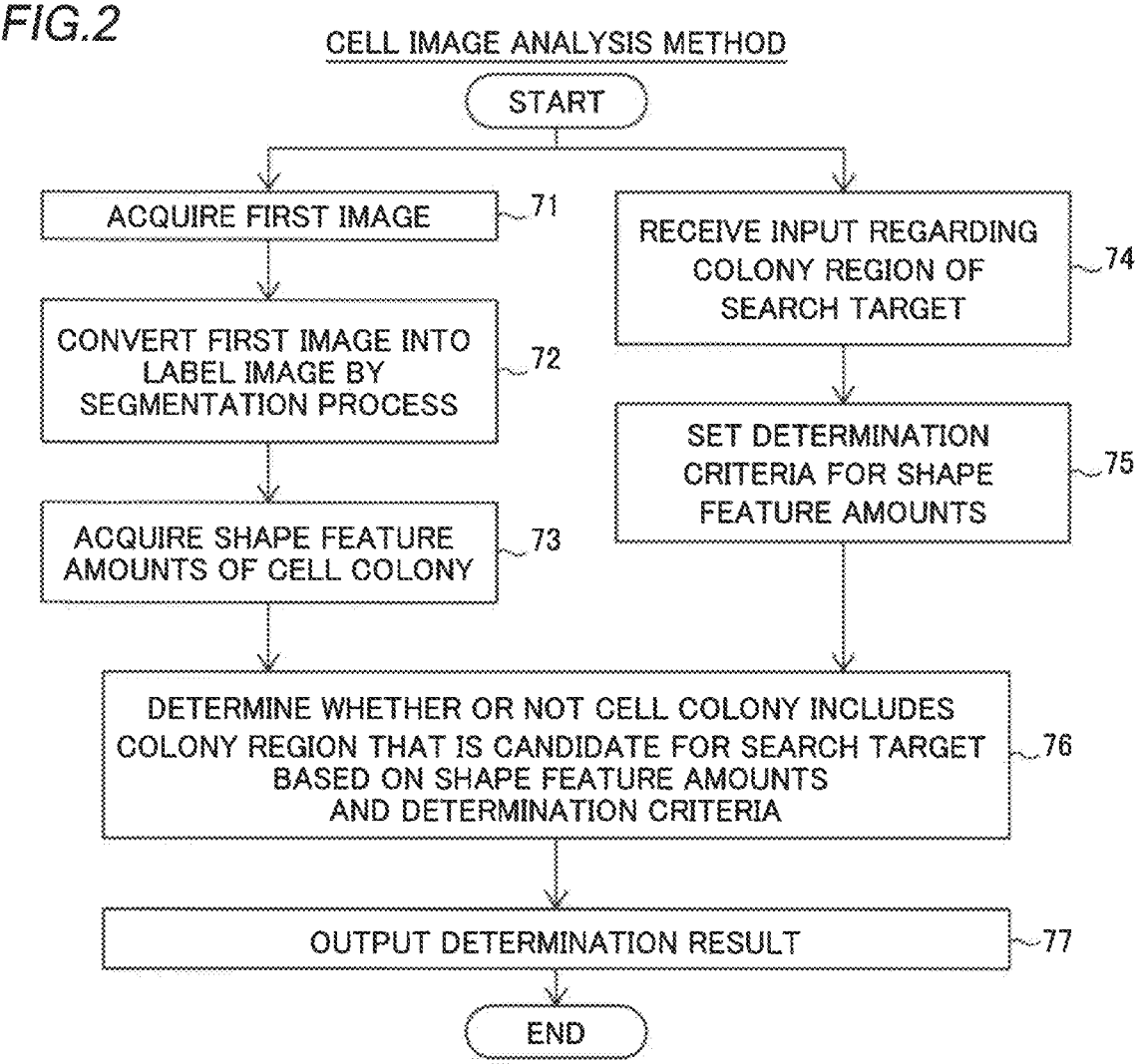
FIG. 2 is a flowchart illustrating the cell image analysis method.

As shown in FIGS. 1 and 2, the cell image analysis method according to this embodiment includes at least the following steps 71 to 76.

(Step 71) A first image 21 of the cell colony 10 including cells having differentiation potential is acquired.

(Step 72) In the cell colony 10 in the first image 21, a segmentation process is performed to identify the colony region 12 of cells (undifferentiated deviant cells) that have already started differentiation and the colony region 11 of undifferentiated cells, and the first image 21 is converted into a label image 21A.

(Step 73) The shape feature amounts 25 of the cell colony 10 are acquired from the label image 21A.

(Step 74) A computer is used to receive an input regarding the colony region of a search target from the user.

(Step 75) Determination criteria 30 for the shape feature amounts 25 are set based on the user's input.

(Step 76) It is determined whether or not each cell colony 10 includes a colony region that is a candidate for a search target based on the shape feature amounts 25 and the determination criteria 30.

In step 71, the first image 21 may be a microscope image of the cell colony 10 including cells having differentiation potential. The microscope image is acquired by an optical microscope such as a transmission observation microscope or a phase-contrast microscope. The first image 21 may be a holographic microscope image. The first image 21 is not particularly limited as long as it is an image obtained by nondestructively imaging the shape of the cell colony 10 at an observable magnification.

The first image 21 is obtained by imaging at least one cell colony 10. The first image 21 is acquired by imaging the cell colony 10 in the culture vessel 90 with an imager 200, as shown in FIG. 1, for example. The culture vessel 90 is a transparent flat dish-shaped culture dish such as a so-called petri dish or a microplate (well plate) in which a plurality of wells are formed.

In step 72 of FIG. 2, the segmentation process is performed on the acquired first image 21. In this description, the "segmentation process" refers to a process to divide an image into a plurality of regions and a process to segment an input image into a plurality of label regions by assigning a label indicating a detection target to a region in which the detection target appears. Each of the label regions refers to a region (a portion of an image) including a group of pixels with a common label in an image. The segmentation process is achieved by an image process using a computer.

The label is information representing the meaning indicated by an image portion including the label region. Segmentation is performed by assigning a label to each pixel in an image. The label may be assigned in units of a group of a plurality of pixels (pixel group). The type of label is called a class.

As shown in FIG. 1, the segmentation process on the first image 21 produces the label image 21A in which the first image 21 has been divided into a plurality of label regions.

The segmentation process in step 72 divides the first image 21 into at least the label region of the colony region 12 of cells (undifferentiated deviant cells) that have started differentiation and the label region of the colony region 11 of undifferentiated cells. That is, classification into at least two classes is performed. Thus, the generated label image 21A includes at least two label regions of the colony region 12 of undifferentiated deviant cells and the colony region 11 of undifferentiated cells. The label image 21A includes three (three classes) label regions of the colony region 12 of undifferentiated deviant cells, the colony region 11 of undifferentiated cells, and a background region 13 other than the colony regions, for example.

In the label image 21A, each pixel in the same label region is represented by the same pixel value or the same color. Different label regions are represented by different pixel values or different colors. The label image 21A according to an example of FIG. 1 is a three-valued image in which each pixel in the first image 21 has been segmented by any of three pixel values corresponding to the three classes of labels (the colony region of undifferentiated deviant cells, the colony region of undifferentiated cells, and the background region). Thus, image information irrelevant to the shape of the cell colony, such as the pattern of the colony region or the light-dark gradation appearing in the first image 21, is removed, and only the shape of each label region can be accurately extracted.

In step 73, the shape feature amounts 25 of the cell colony 10 are acquired from the label image 21A. The shape feature amounts 25 refer to information that numerically expresses the shape of the cell colony 10 in the label image 21A. The shape feature amounts 25 may be amounts (numerical values) indicating the size, contour shape, width, length, etc. of the label region indicating the cell colony 10. The shape feature amounts 25 of the cell colony 10 may be shape feature amounts related to the entire region of the cell colony 10, or shape feature amounts related to the colony region 11 of undifferentiated cells or the colony region 12 of undifferentiated deviant cells, which is a portion of the cell colony 10. The specific contents of the shape feature amounts 25 are described below.

In step 74, the input regarding the colony region of a search target is received via an input device provided in the computer. Then, in step 75, the determination criteria 30 for the shape feature amounts 25 are set by the computer based on the input information.

The information regarding the colony region of a search target is information for setting the determination criteria 30 for the shape feature amounts 25. The information regarding the colony region of a search target may be the determination criteria 30 themselves. The information regarding the colony region of a search target may be information showing the user's tendency as to what kind of colony region the user determines as a search target. More simply, the information regarding the colony region of a search target may be information indicating the user's preference regarding the cell colony 10 as to what kind of colony region the user desires. Therefore, the determination criteria 30 for the shape feature amounts 25 according to the user's own determination criteria are set based on the input regarding the colony region of a search target.

The determination criteria 30 for the shape feature amounts 25 set based on the user's input may be thresholds of the shape feature amounts 25, for example. When the determination is made using a plurality of shape feature amounts 25, the determination criteria 30 may include weights for the individual shape feature amounts 25 used in the determination. For example, the user inputs and sets the thresholds or the weights of the shape feature amounts 25 according to the features of the cell colony 10 to be picked. A sample microscope image may be prepared in advance, and the user himself/herself may select and input (teach) whether or not each cell colony 10 appearing in the microscope image includes a colony region that is a candidate for a search target such that the determination criteria 30 are set.

In step 76, it is determined for each cell colony 10 appearing in the image whether or not each individual cell colony 10 in the first image 21 (label image 21A) includes the colony region that is a candidate for a search target. The determination process is achieved by an image process using a computer.

The determination process to determine whether or not the cell colony 10 includes the colony region that is a candidate for a search target is performed depending on whether or not the shape feature amounts 25 acquired for the cell colony 10 to be determined match the determination criteria 30 for the shape feature amounts 25.

As a result of step 76, a determination result 35 is generated as to whether or not each cell colony 10 in the first image 21 (label image 21A) includes the colony region that is a candidate for a search target. The determination result 35 may be binary information of "including the colony region that is a candidate for a search target (positive example)" or "not including the colony region that is a candidate for a search target (negative example)". As described below, the determination result 35 may be information indicating the degree of possibility of "including the colony region that is a candidate for a search target".

In step 77, the determination result 35 is output. Based on the determination result 35, it can be determined by the user himself/herself or automatically whether or not each individual cell colony 10 in the first image 21 (label image 21A) is to be picked. For example, the user selects the cell colony 10 according to the purpose as a picking target from cell colonies 10 determined to be a positive example in consideration of the determination result 35 of the individual cell colony 10. Furthermore, for example, from the cell colonies 10 determined to be a positive example, any cell colony 10 is selected as a picking target by an automatic process such as a threshold process. Therefore, the user can determine the picking target without performing a search operation such as confirming the morphology of each cell colony 10 in the culture vessel 90 in detail in the picking operation.

Cell Image Analyzer

The outline of the cell image analyzer 100 according to this embodiment is described with reference to FIG. 3. The cell image analyzer 100 executes the cell image analysis method shown in FIGS. 1 and 2.

Figure 3:
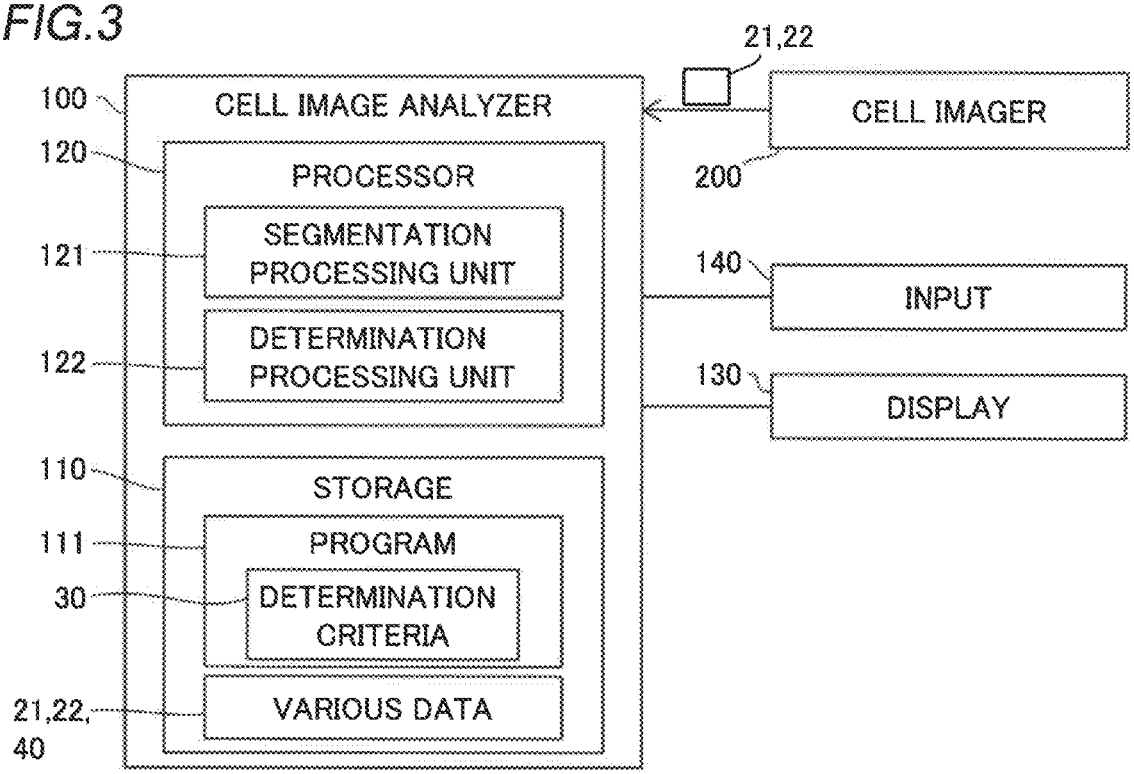
FIG. 3 is a block diagram showing the outline of a cell image analyzer according to the embodiment.

The cell image analyzer 100 shown in FIG. 3 includes a storage 110, a segmentation processing unit 121, a determination processing unit 122, and an input 140. The cell image analyzer 100 can acquire a microscope image from a cell imager 200 by an input and an output of a signal, data communication, or data transfer via a recording medium.

A microscope image of the cell colony 10 including cells having differentiation potential is input to the storage 110. The microscope image is the first image 21 shown in FIG. 1. The cell image analyzer 100 stores image data of the first image 21 acquired from the cell imager 200 in the storage 110. Thus, step 71 of FIG. 2 is carried out.

The segmentation processing unit 121 performs a segmentation process to identify the colony region 12 of cells that have already started differentiation and the colony region 11 of undifferentiated cells in the cell colony 10 in the microscope image (first image 21). That is, the segmentation processing unit 121 carries out step 72 of FIG. 2. The segmentation processing unit 121 converts the first image 21 into the label image 21A (see FIG. 1) by the segmentation process on the first image 21.

The determination processing unit 122 determines whether or not each cell colony 10 included in the microscope image includes the colony region that is a candidate for a search target.

The determination processing unit 122 acquires the shape feature amounts 25 (see FIG. 1) of the cell colony 10 from the label image 21A, and determines the colony region based on the shape feature amounts 25 and the determination criteria 30 for the shape feature amounts 25. That is, the determination processing unit 122 carries out step 73 and step 76 of FIG. 2. The determination criteria 30 for the shape feature amounts 25 are set in the cell image analyzer 100 based on the user's input using the input 140 in step 74 and step 75 prior to the determination process (step 76), and are stored in the storage 110.

The determination processing unit 122 outputs the determination result 35 in step 77 of FIG. 2. Based on the determination result 35, it can be determined by the user or automatically whether or not each individual cell colony 10 in the first image 21 (label image 21A) is to be picked.

In an example shown in FIG. 3, the cell image analyzer 100 includes a personal computer (PC) including a processor 120 that performs an arithmetic process such as a central processing unit (CPU), a graphics processing unit (GPU), or a field-programmable gate array (FPGA), the storage 110 that stores data, and the input 140.

In the example of FIG. 3, the processor 120 functions as the segmentation processing unit 121 and the determination processing unit 122 by executing a program 111 stored in the storage 110. That is, in the example of FIG. 3, the segmentation processing unit 121 and the determination processing unit 122 are achieved as functional blocks of the processor 120. The segmentation processing unit 121 and the determination processing unit 122 may be configured as separate hardware.

The individual hardware refers to the segmentation processing unit 121 and the determination processing unit 122 configured by separate processors. Furthermore, the individual hardware refers to a plurality of computers (PCs) of the cell image analyzer 100, one of which performs a segmentation process and the other of which performs a determination process, and both of which are separately provided.

The storage 110 may include a volatile and/or non-volatile storage device. For example, the storage 110 includes a hard disk drive or a solid state drive. The program 111 of the cell image analyzer 100 is stored in the storage 110. The storage 110 stores various data such as the acquired microscope image (first image 21).

The input 140 receives an operation input from the user. The input 140 includes an input device such as a mouse or a keyboard. Thus, the input 140 receives an input regarding the colony region of a search target. Furthermore, the cell image analyzer 100 is connected to a display 130 that displays an image. The display 130 includes a liquid crystal monitor or an organic/inorganic EL monitor, for example. The input 140 may be a touch panel integrated with the display 130.

The cell image analyzer 100 can set the determination criteria 30 by receiving the user's operation input via the input 140. The cell image analyzer 100 can display the microscope image (first image 21), the label image 21A, the determination result 35, etc. on the display 130. The cell image analyzer 100 receives an input of a selection operation on the label image 21A displayed on the display 130, for example. Thus, the cell image analyzer 100 is configured to allow the user to identify the picking target (the cell colony 10 including the colony region that is a candidate for a search target).

Setting of Determination Criteria

An example of a method for setting the determination criteria 30 is now described. The determination criteria 30 can be automatically set from the input information by receiving the operation input from the user.

For example, step 74 of receiving the input regarding the colony region of a search target includes a step of receiving, from the user, an input of selection information 40 as to whether or not the cell colony 10 in a second image 22 acquired in advance includes a desired colony region. Then, in step 75 of setting the determination criteria 30, the determination criteria 30 are set based on the received selection information 40.

The second image 22 is a microscope image acquired in advance as a sample for setting the determination criteria 30. The second image 22 is an image of the cell colony 10 including cells having differentiation potential, similarly to the first image 21 (see FIG. 1).

The selection information 40 is information selected by the user as to whether the cell colony 10 in the second image 22 is a positive example (includes a desired colony region) or a negative example (does not include a desired colony region). That is, the selection information 40 is one-to-one associated with one cell colony 10 in the second image 22, and indicates whether the associated cell colony 10 is a positive example or a negative example. The selection information 40 is binary information indicating either a positive example ("1", for example) or a negative example ("0", for example).

The selection information 40 is acquired by receiving a user's selection of an image displayed on the display 130 via the input 140, for example. In this embodiment, the step of receiving the input of the selection information 40 includes allowing the user to specify a colony region in the second image 22 or a label image 22A of the second image 22, or allowing the user to pick the colony region. Thus, the user actually specifies the colony region or the user actually picks the colony region such that the selection information 40 can be input.

Figure 6:
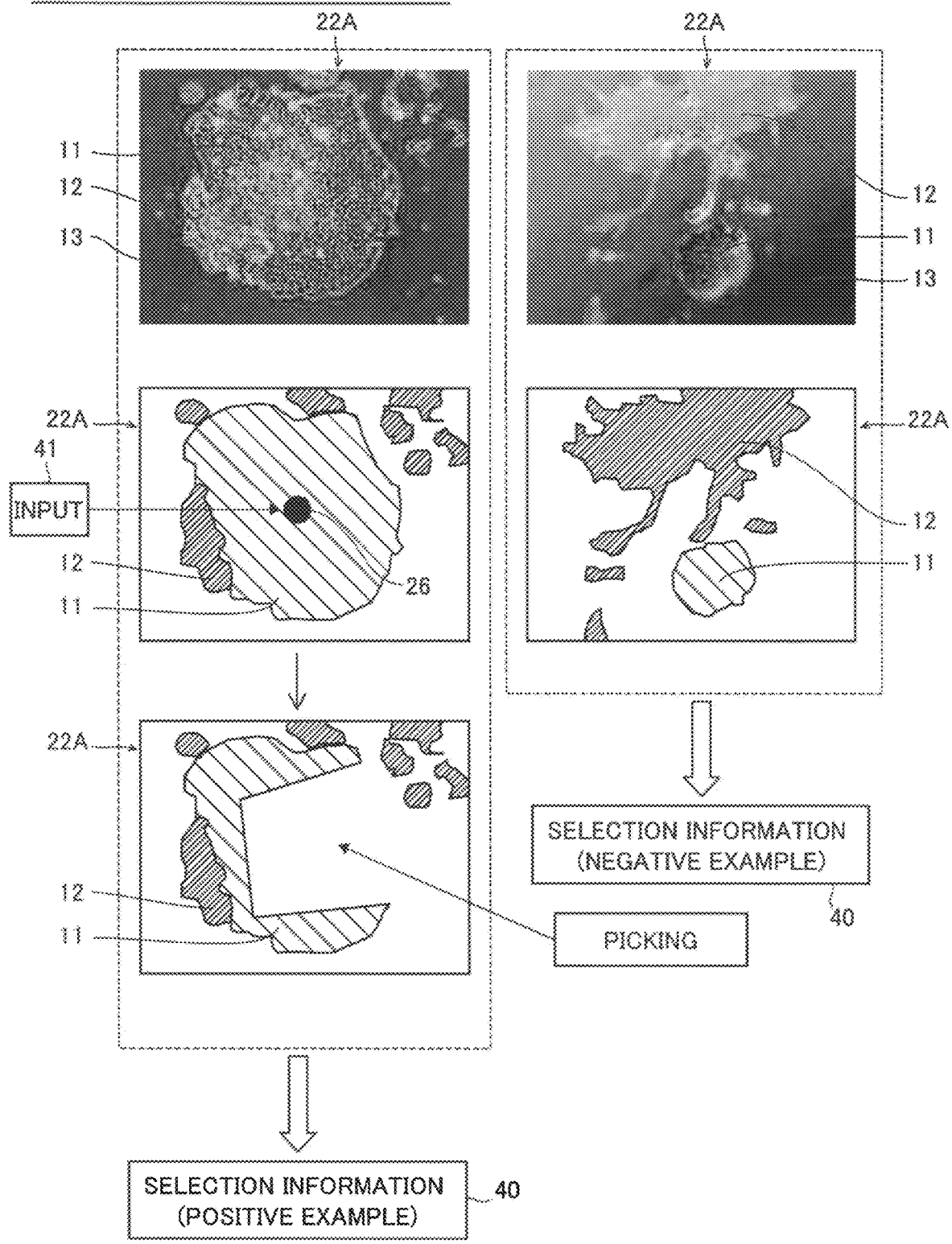
FIG. 6 is a diagram illustrating a selection information input method.

FIG. 6 shows an example of an input of an operation on the label image 22A of the second image 22. In FIG. 6, the label image 22A and a schematic view for explanation are shown side by side. In the second image 22 or the label image 22A of the second image 22, the user performs an operation input 41 to select the cell colony 10 as a positive example via the input 140 (see FIG. 3). Alternatively, the user actually picks the cell colony 10 as a positive example in a state in which the second image 22 or the label image 22A of the second image 22 is displayed. As a result of picking, the cell colony 10 is removed from the image such that the selection information 40 indicating that the removed cell colony 10 is a positive example can be acquired. The cell colony 10 to which no input has been provided is given the selection information 40 as a negative example. An operation input indicating that it is a negative example may be provided to the cell colony 10 that the user determines to be a negative example.

The selection information 40 is generated based on the user's operation input for an appropriate number of cell colonies 10. From a plurality of pieces of generated selection information 40, it is possible to obtain the user's tendency (i.e., preference information) as to what kind of cell colony 10 is determined as a positive example. Consequently, the determination criteria 30 are set based on the received selection information 40.

First Trained Model

Figure 4:
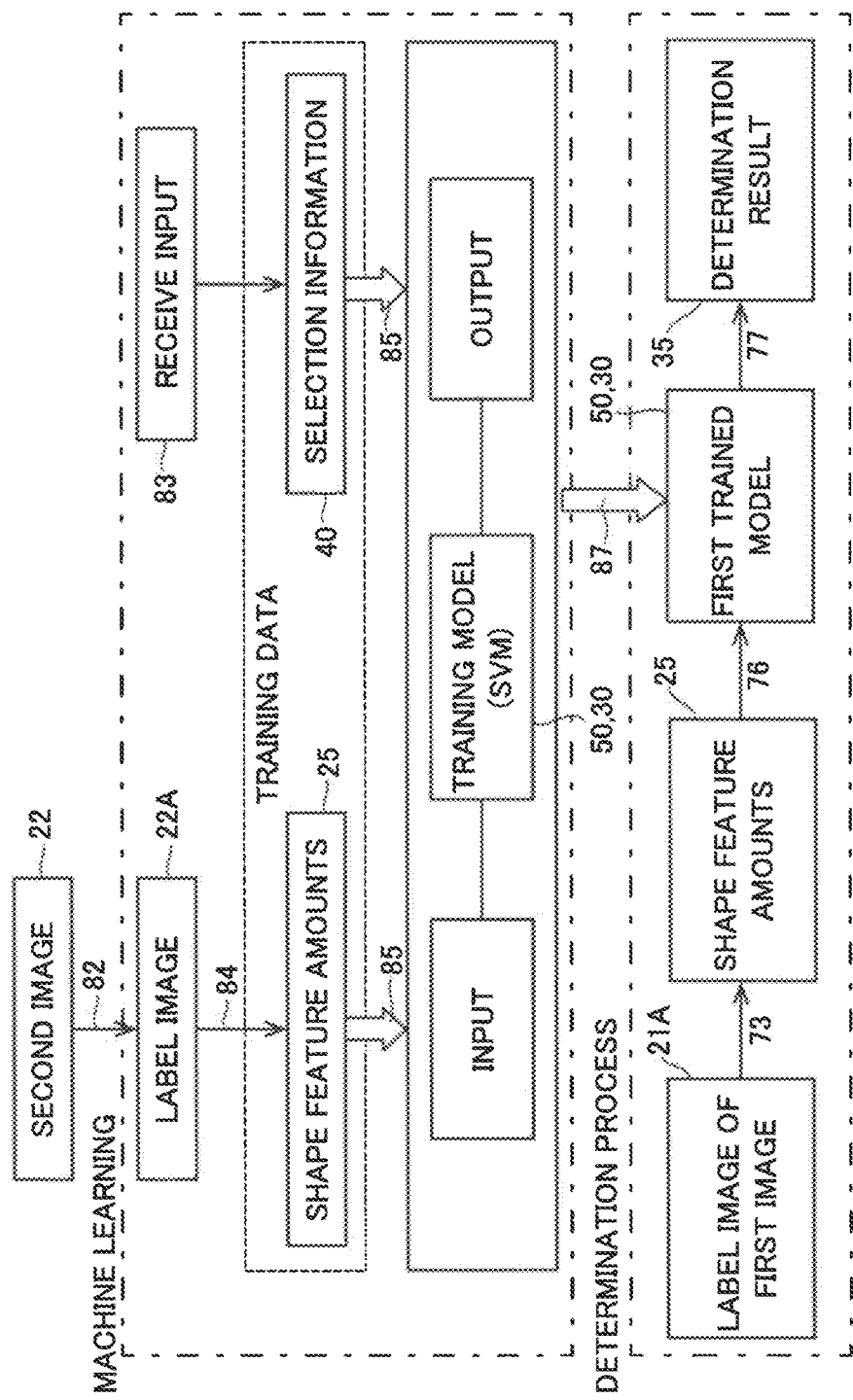
FIG. 4 is a diagram illustrating a first trained model.

In this embodiment, the determination criteria 30 may be acquired by machine learning using the selection information 40. That is, step 75 of setting the determination criteria 30 includes creating a first trained model 50 that has acquired the determination criteria 30 for the shape feature amounts 25 by machine learning using the shape feature amounts 25 acquired from the label image 22A of the second image 22 as input data and the selection information 40 as teaching data, as shown in FIG. 4. Furthermore, step 76 (see FIG. 2) of determining whether or not the cell colony 10 includes the colony region that is a candidate for a search target includes inputting the shape feature amounts 25 acquired from the label image 21A of the first image 21 to the first trained model 50 to generate the determination result 35.

The label image 22A of the second image 22 is acquired by the segmentation process on the second image 22, similarly to the label image 21A of the first image 21 shown in FIG. 1. The label image 22A of the second image 22 is divided into a plurality of regions, similarly to the label image 21A of the first image 21. That is, the label image 22A (see FIG. 6) of the second image 22 includes at least the colony region 12 of undifferentiated deviant cells and the colony region 11 of undifferentiated cells.

From the label image 22A of the second image 22, the shape feature amounts 25 are calculated for each cell colony 10. For each cell colony 10 appearing in the second image 22, the shape feature amounts 25 of the cell colony 10 and the selection information 40 regarding the cell colony 10 are acquired. When the shape feature amounts 25 of the cell colony 10 of interest are given by machine learning using the shape feature amounts 25 as input data and the selection information 40 as teaching data, it is learned to determine whether or not the cell colony 10 is a positive example (includes the colony region that is a candidate for a search target). That is, the first trained model 50 that has acquired the determination criteria 30 for the shape feature amounts 25 is generated by machine learning.

The first trained model 50 (training model for the determination process) is a support vector machine (SVM), for example. Preferably, the first trained model 50 is a non-linear SVM. The first trained model 50 generates the determination result 35 as to whether or not the cell colony 10 corresponds to a positive example, using the shape feature amounts 25 of an unknown cell colony 10 appearing in the label image 21A of the first image 21 as an input. The first trained model 50 generates, in a range of 0(%) to 100(%), a certainty that is the degree of possibility that the cell colony 10 of interest corresponds to a positive example as the determination result 35, for example.

Figure 5:
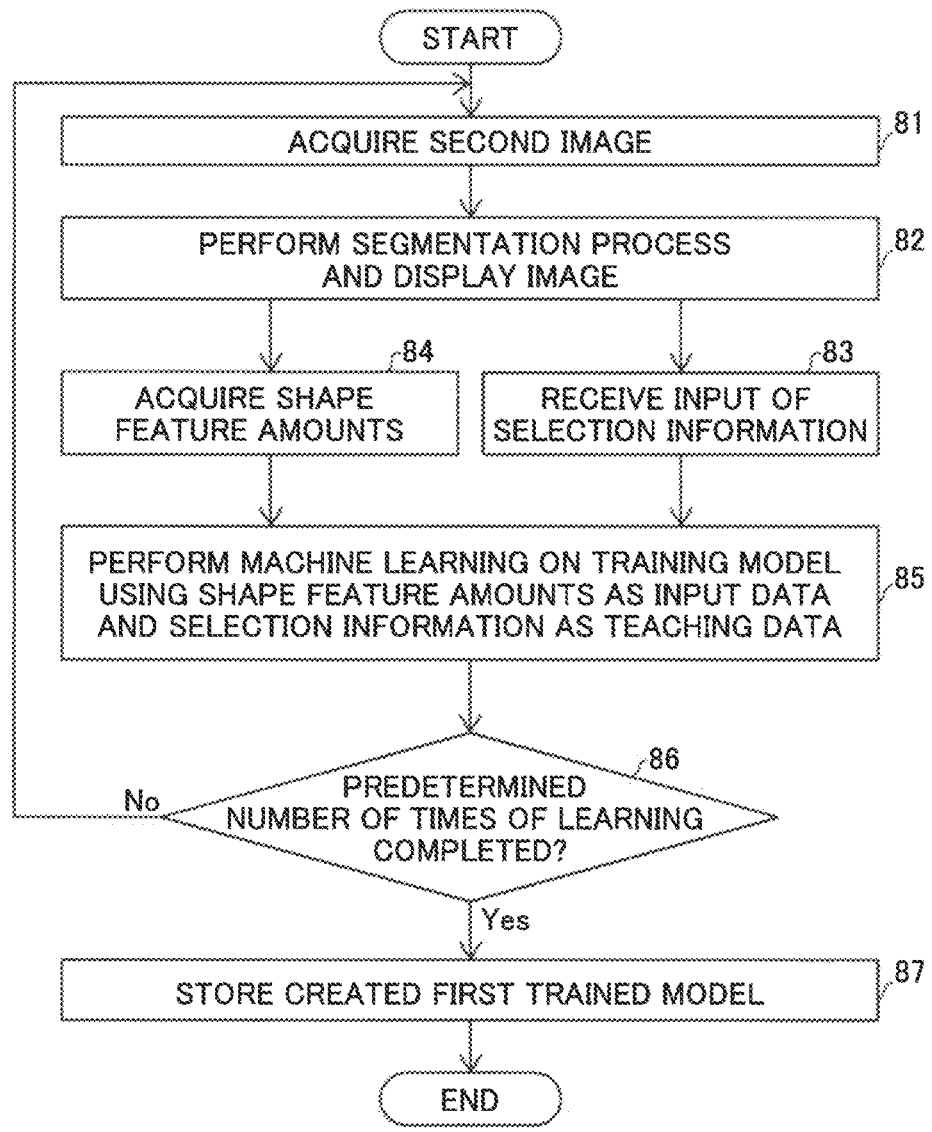
FIG. 5 is a flowchart illustrating a creation process for a first trained model.

FIG. 5 shows a creation process for the first trained model 50. The first trained model 50 can be created by the cell image analyzer 100 shown in FIG. 3, for example.

In step 81, the second image 22 is acquired from the cell imager 200 and input to the storage 110.

In step 82, the segmentation processing unit 121 performs the segmentation process on the second image 22. The segmentation process produces the label image 22A of the second image 22.

In step 83, the input of the selection information 40 to the cell colony 10 in the label image 22A is received by the input 140. This step 83 is an example of a "step of receiving the input of the selection information from the user" in the cell image analysis method according to this embodiment. Furthermore, in step 84, the determination processing unit 122 calculates the shape feature amounts 25 of the cell colony 10 to which the selection information 40 has been input.

In step 85, the determination processing unit 122 performs machine learning using the shape feature amounts 25 as input data and the selection information 40 as teaching data. Step 85 is an example of a "step of setting the determination criteria" in the cell image analysis method according to this embodiment.

In step 86, it is determined whether or not a predetermined number of times of learning are completed. When a predetermined number of times of leaning are not completed, the process returns to step 81, and the determination processing unit 122 learns about the next cell colony 10. When a predetermined number of times of learning are completed, machine learning is completed. In step 87, the created first trained model 50 is stored in the storage 110.

Thus, the creation process for the first trained model 50 that has acquired the determination criteria 30 for the shape feature amounts 25 is performed. Thus, as shown in FIG. 4, in the determination process (step 76 of FIG. 2), the determination processing unit 122 calculates the shape feature amounts 25 from the label image 21A of the first image 21, and inputs them to the first trained model 50. Consequently, the determination processing unit 122 generates the determination result 35 by the first trained model 50. The machine learning and the determination process using such shape feature amounts 25 require a smaller amount of input data as compared with a case in which the entire image is used as input data, for example, and thus high-speed processing with a small processing load is possible. Therefore, the machine learning of the first trained model 50 in which the user is involved can be completed in a short time, and the process can be quickly performed until the determination result 35 is output during the picking operation.

Shape Feature Amounts

The shape feature amounts 25 are now described.

As shown in FIG. 7, the shape feature amounts 25 include a shape feature amount related to at least one of i) the entire region of the cell colony 10 included in the label image 21A, ii) the colony region 11 of undifferentiated cells included in the cell colony 10, or iii) the colony region 12 of cells (undifferentiated deviant cells) that have started differentiation included in the cell colony 10. In FIG. 7, for convenience, the shape feature amounts 25A of the entire region of the cell colony 10 are referred to as "colony feature amounts", the shape feature amounts 25B of the colony region 11 of undifferentiated cells are referred to as "undifferentiated region feature amounts", and the shape feature amounts 25C of the colony region 12 of undifferentiated deviant cells are referred to as "deviant region feature amounts".

In this embodiment, the first image 21 (second image 22) is divided into three classes of labels: the colony region 11 of undifferentiated cells, the colony region 12 of undifferentiated deviant cells, and the background region 13. Therefore, as shown in FIG. 8, the entire region of the cell colony 10 is the sum of the colony region 11 of undifferentiated cells and the colony region 12 of undifferentiated deviant cells. FIG. 8 shows a cell colony 10 including the colony region 11 and the colony region 12, but there are also a cell colony 10 including only the colony region 11 of undifferentiated cells and a cell colony 10 including only the colony region 12 of undifferentiated deviant cells.

As shown in FIG. 7, the shape feature amounts 25 specifically include at least one of i) the area of the region, ii) the contour length of the region, iii) the degree of circularity of the region, iv) the aspect ratio of the minimum circumscribed rectangle of the region, or v) the area ratio of the colony region 11 to the entire region of the cell colony 10. The term "region" here refers to any one of the entire region of the cell colony 10, the colony region 11, and the colony region 12.

The "area of the region" corresponds to the number of pixels included in the region of interest. The "contour length of the region" corresponds to the number of pixels of the contour 91 of the region of interest. The "degree of circularity of the region" is a feature amount in which as the contour 91 of the region of interest is closer to a circle, the value is closer to 1. Assuming that the area of the region of interest is S and the contour length of the region of interest is C, the degree of circularity R of the region is represented by $R=4\pi \times (S/C^2)$.

The "aspect ratio of the minimum circumscribed rectangle of the region" is represented by the (short side/long side) of the minimum circumscribed rectangle 92 of the region of interest. The minimum circumscribed rectangle 92 is a rectangle having the smallest area among rectangles surrounding the region of interest. The "area ratio of the colony region 11 to the entire region of the cell colony 10" is a ratio occupied by the colony region 11 of undifferentiated cells in the cell colony 10. The area ratio is represented by (the area of the colony region 11 of undifferentiated cells/the area of the entire cell colony 10).

FIG. 7 shows examples of the shape feature amounts 25 that may be used when the colony region 11 of undifferentiated cells is picked during passaging. As the shape feature amounts 25A (colony feature amounts) related to the entire region of the cell colony 10, the area of the entire region of the cell colony 10, the contour length of the entire region of the cell colony 10, the degree of circularity of the entire region of the cell colony 10, and the aspect ratio of the entire region of the cell colony 10 can be used.

As the shape feature amounts 25B (undifferentiated region feature amounts) related to the colony region 11 of undifferentiated cells, the area of the colony region 11 of undifferentiated cells, the contour length of the colony region 11 of undifferentiated cells, the degree of circularity of the colony region 11 of undifferentiated cells, and the aspect ratio of the colony region 11 of undifferentiated cells can be used.

As the shape feature amounts 25C (deviant region feature amounts) related to the colony region 12 of undifferentiated deviant cells, the area of the colony region 12 of undifferentiated deviant cells and the area ratio of the colony region 11 to the entire region of the cell colony 10 can be used. The area ratio indicates that as the value is larger, the colony region 12 of undifferentiated deviant cells is smaller, and becomes a measure of the low proportion of the undifferentiated deviant cells when the colony region 11 of undifferentiated cells is picked.

The shape feature amounts 25 used in the determination process include one or more of the above feature amounts. The features of the cell colony 10 that the user actually uses as criteria to determine whether or not the cell colony 10 is to be picked are not single, and thus it is preferable to use a plurality of shape feature amounts 25 for the determination process. For example, in the determination process, at least one of the shape feature amounts 25A related to the entire region of the cell colony 10, at least one of the shape feature amounts 25B related to the colony region 11 of undifferentiated cells, and at least one of the shape feature amounts 25C related to the colony region 12 of undifferentiated deviant cells are used. As the number of shape feature amounts 25 increases, it becomes more difficult to set appropriate determination criteria 30. The first trained model 50 by machine learning shown in FIG. 4 is used such that it is not necessary to directly obtain an appropriate threshold for each shape feature amount 25 even when a plurality of shape feature amounts 25 are used, and the comprehensive determination criteria 30 can be obtained, and thus it is preferable to use the first trained model 50 by machine learning shown in FIG. 4.

Second Trained Model

Figure 9:
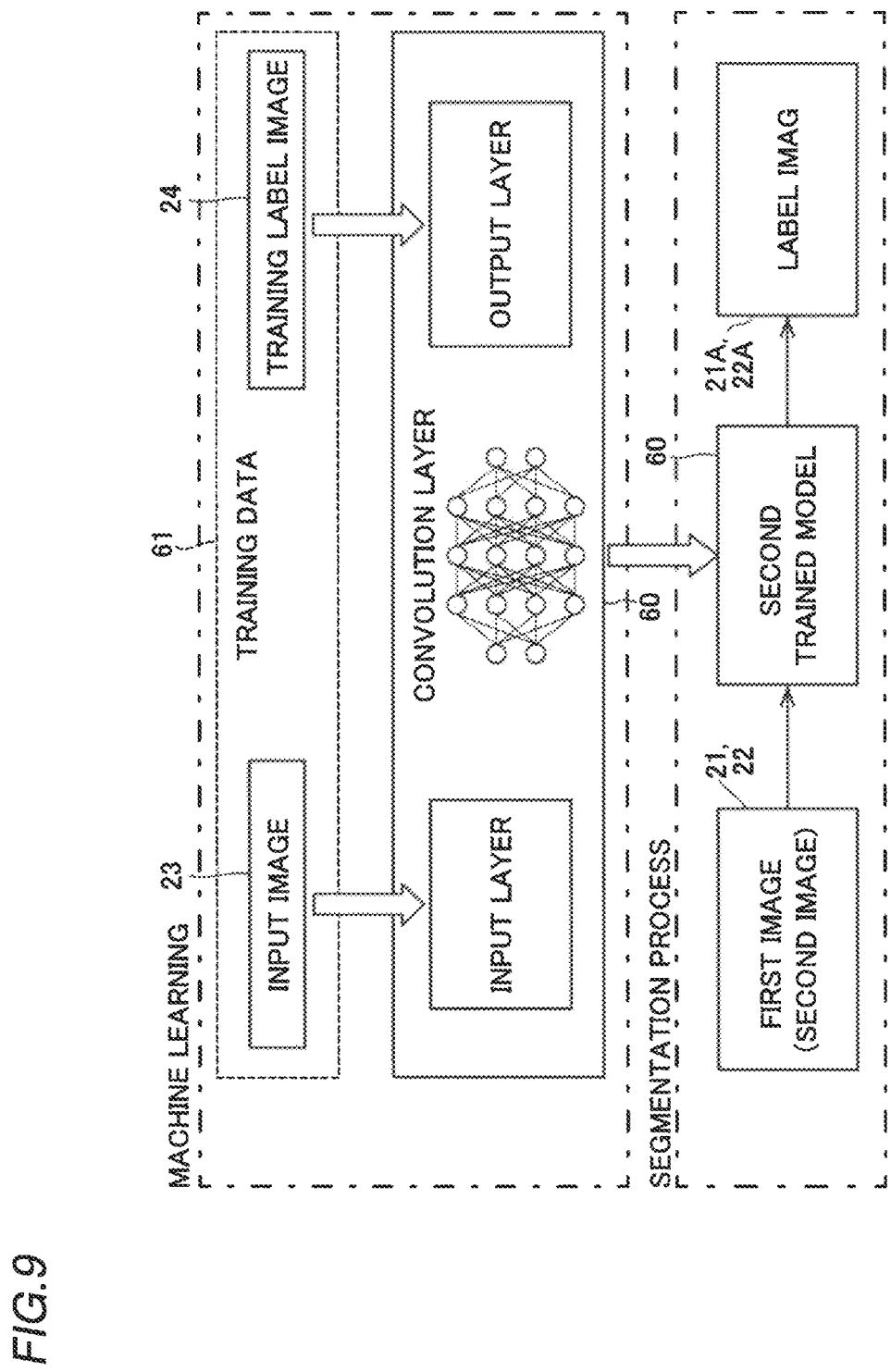
FIG. 9 is a diagram illustrating a second trained model.

In this embodiment, the segmentation process shown in step 72 of FIG. 2 may be performed by a second trained model 60 (see FIG. 9) in which the segmentation process has been machine-learned. That is, step 72 of converting the first image 21 into the label image 21A includes generating the label image 21A by the second trained model 60 that assigns a segmentation result label to the colony region 11, using the first image 21 as input data, as shown in FIG. 9.

The second trained model 60 performs the segmentation process on the input image (the first image 21 or the second image 22), and outputs the label image (the label image 21A or the label image 22A) divided into a plurality of label regions. As a machine learning method, any method such as a fully convolutional network (FCN), a neural network, a support vector machine (SVM), or boosting can be used. For the second trained model 60 in this embodiment, from the viewpoint of the identification performance of the label regions, it is preferable to use a convolutional network frequently used for semantic segmentation, and it is more preferable to use a fully convolutional network. Such a second trained model 60 includes an input layer to which an image is input, a convolution layer, and an output layer.

Figure 10:
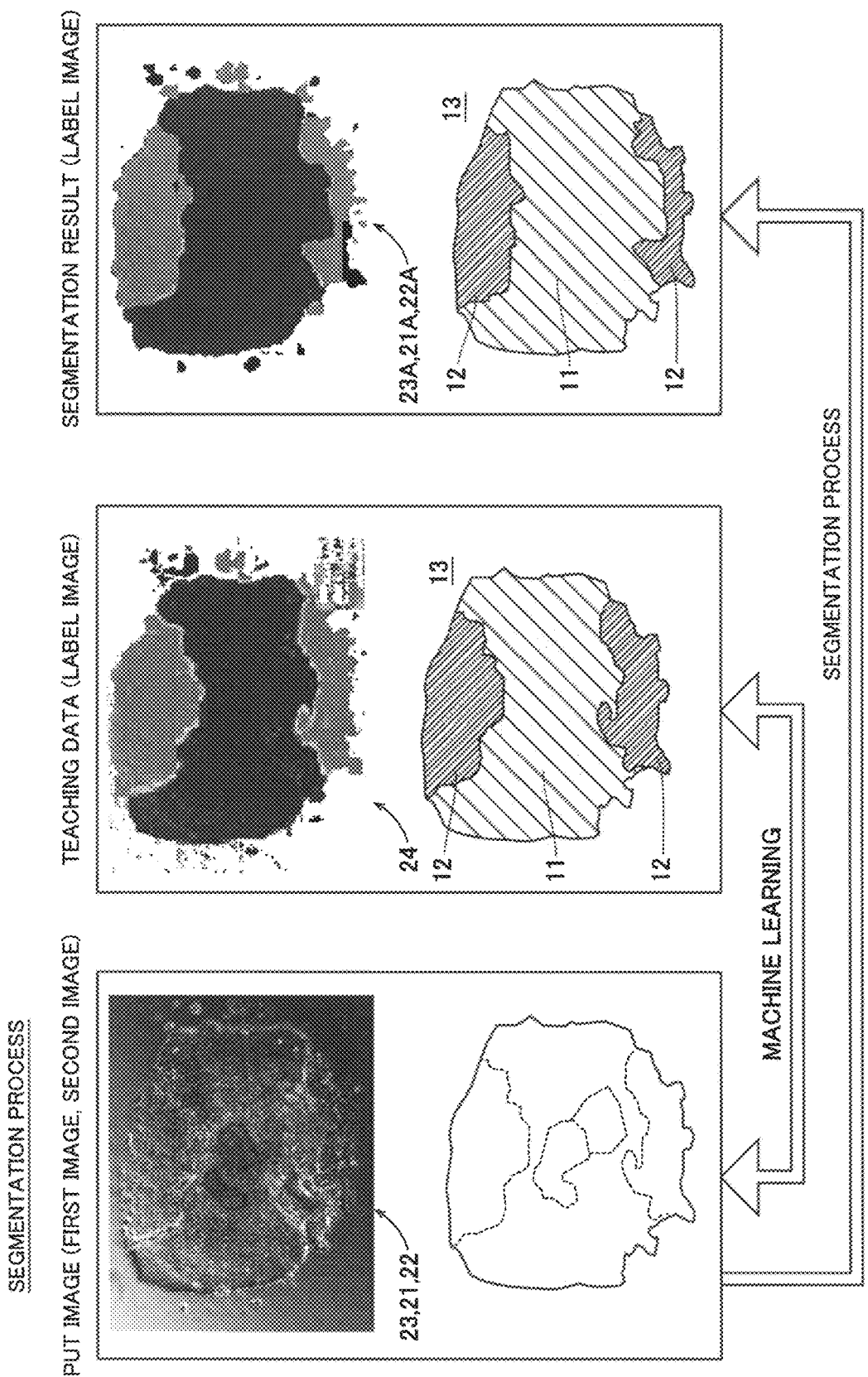
FIG. 10 is a diagram showing examples of an input image, a training label image, and a segmentation result label image in machine learning.

In order to create the second trained model 60, machine learning is performed using a training data set that includes a plurality of pieces of training data 61. FIG. 10 shows an input image 23, a training label image 24 as teaching data, and a label image 23A as a result of performing the segmentation process on the input image 23 by the second trained model 60 after machine learning. The training label image 24 and the label image 23A are labeled in three classes: the colony region 11 of undifferentiated cells, the colony region 12 of undifferentiated deviant cells, and the background region 13. Each image is actually colored, and the label image is color-coded into three colors. However, it is grayscaled for convenience, and thus each image and a schematic view showing the cell colony 10 are shown side by side for the sake of explanation.

The training data 61 used for machine learning includes the input image 23 and the training label image 24 for the same cell colony 10. The input image 23 is an original image before the segmentation process is performed, and is an image showing the same cell colony 10 as those in the first image 21 and the second image 22. The training label image 24 is created as a correct image to be generated as a result of the segmentation process on the input image 23. That is, the training label image 24 is obtained by dividing the input image 23 into a plurality of label regions.

The training label image 24 is created by the creator of an image for training for performing machine learning. For example, for the cell colony 10, a cell membrane staining image in which a cell region has been stained with a staining agent and a nuclear staining image in which a nuclear staining region of an undifferentiated cell has been stained with an undifferentiated marker are acquired, and after the cell membrane staining image and the nuclear staining image are binarized by a threshold process, a difference between the two images is acquired such that the training label image 24 is created.

As shown in FIGS. 9 and 10, when the second trained model 60 is created, a conversion process (segmentation process) from the input image 23 to the training label image 24, which is a correct answer, is learned by a training model for the segmentation process. As a result of machine learning, the first image 21 or the second image 22 to be processed is input to the created second trained model 60 such that the label image 21A or the label image 22A on which the segmentation process has been performed is generated.

The first trained model 50 for the determination process and the second trained model 60 for the segmentation process as described above are stored in the storage 110 as a portion of the program 111 executed by the processor 120 of FIG. 3, for example. When the processor 120 functions as the determination processing unit 122, the determination process is performed using the first trained model 50. When the processor 120 functions as the segmentation processing unit 121, the segmentation process is performed using the second trained model 60.

Cell Picking System

As a more specific configuration example, a cell picking system 500 including the cell image analyzer 100 according to this embodiment, the cell imager 200, and a cell picking device 300 is described with reference to FIG. 11.

Figure 12:
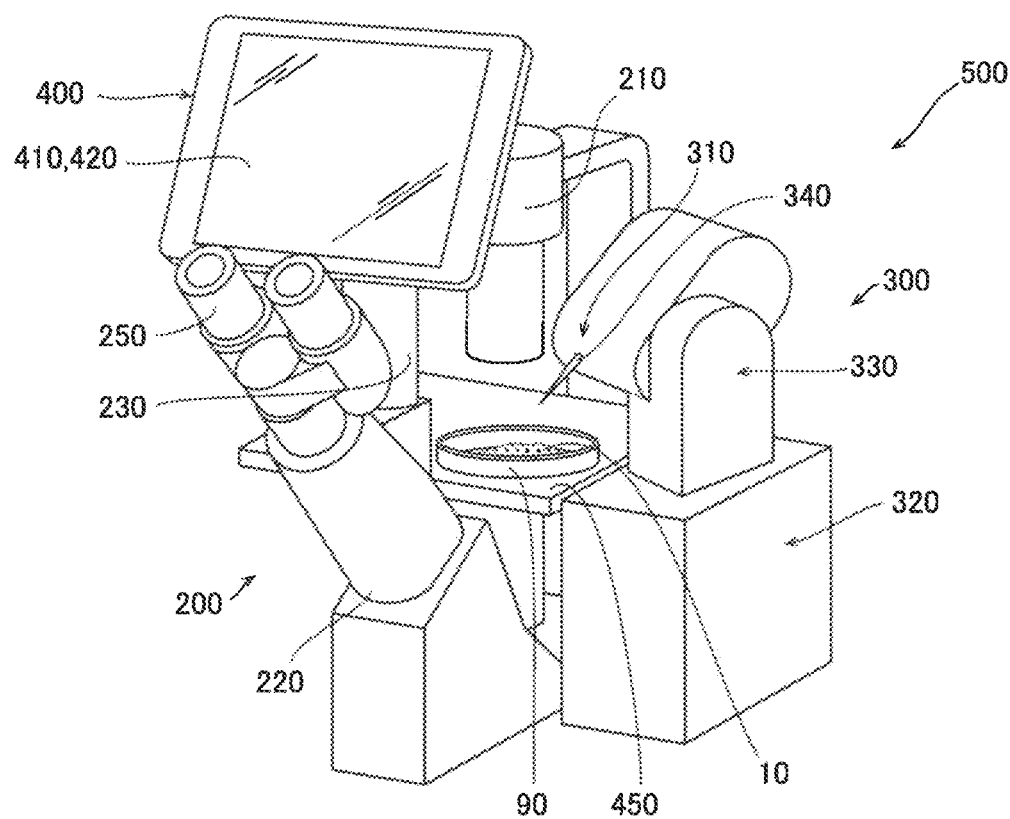
FIG. 12 is a perspective view illustrating the picking system.

The cell picking system 500 is configured to image the cell colony 10 (see FIG. 1) in the culture vessel 90 by the cell imager 200, perform the segmentation process and the determination process on the obtained first image 21, and perform a picking operation automatically or semi-automatically based on the determination result 35. The cell picking system 500 includes a controller 400 configured or programmed to control the picking operation. FIG. 12 shows a configuration example of the cell picking system 500 in which the cell imager 200, the cell picking device 300, and the controller 400 are combined.

Figure 11:
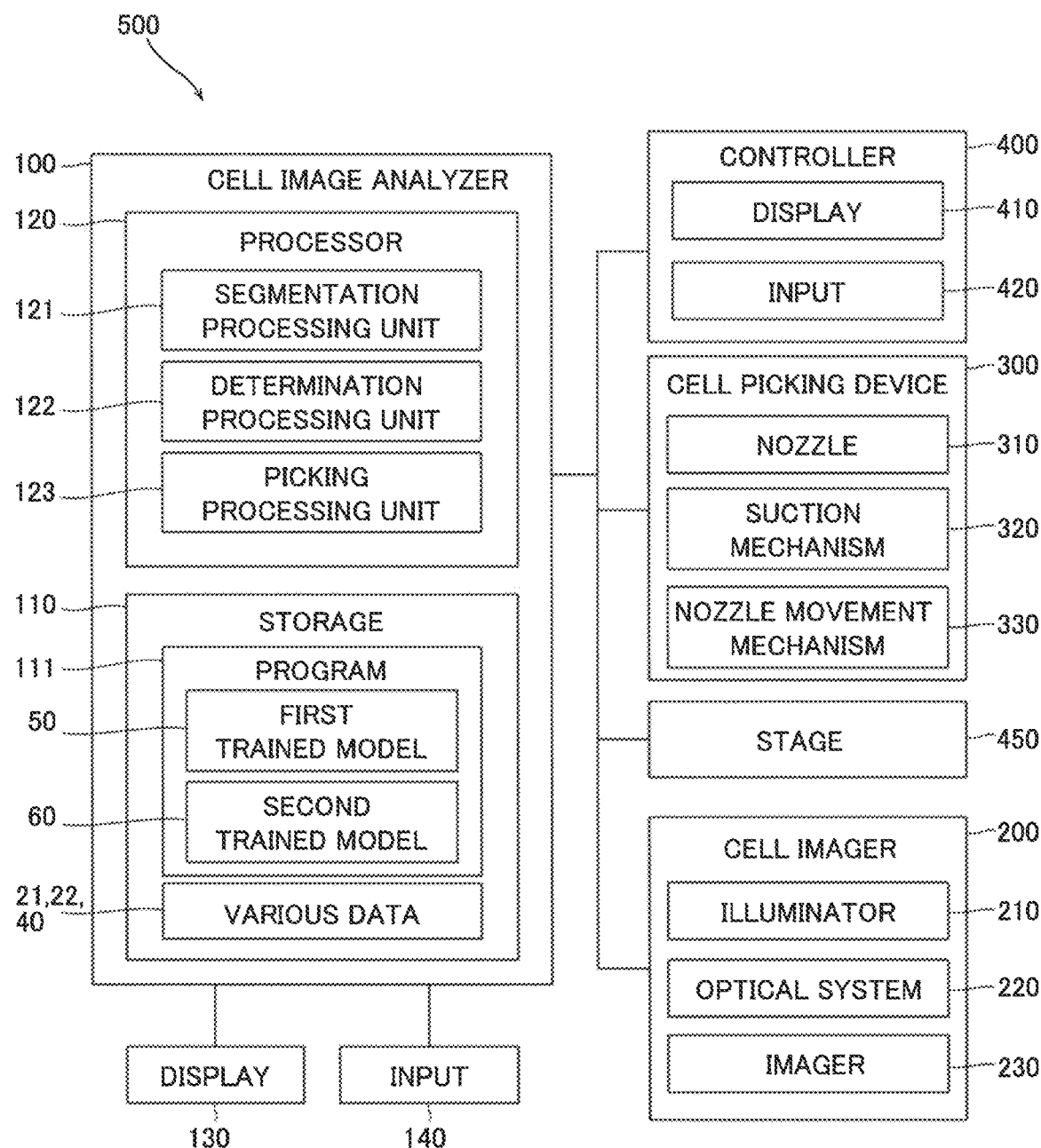
FIG. 11 is a diagram illustrating an example of a picking system including the cell image analyzer.

As shown in FIGS. 11 and 12, the cell imager 200 images the cell colony 10 in the culture vessel 90 and acquires a microscope image (the first image 21 or the second image 22). The cell imager 200 outputs the microscope image to the controller 400. The cell imager 200 includes an illuminator 210, an optical system 220, and an imager 230.

The illuminator 210 irradiates the optical system 220 with illumination light via the culture vessel 90 placed on a stage 450. The illuminator 210 includes a light source such as an LED that generates illumination light in a visible wavelength region. The optical system 220 includes a lens group such as an objective lens and sends incident light transmitted through the culture vessel 90 to the imager 230 to form an image having a desired magnification. The imager 230 includes an image sensor and converts light received through the optical system 220 into an electric signal to generate a microscope image. Examples of the image sensor include a charge-coupled device (CCD) image sensor, a complementary MOS (CMOS) image sensor, etc.

FIG. 12 shows a configuration example in which the imager 230 is attached to an inverted optical microscope (phase-contrast microscope) to form the cell imager 200. The user can confirm the cell colony 10 with the naked eye instead of the image through an eyepiece 250 of the optical microscope.

The controller 400 is a computer including a processor and a storage (not shown), and the processor functions as a controller by executing a program stored in the storage. The controller 400 is communicably connected to the cell image analyzer 100, the cell imager 200, and the cell picking device 300. In an example of FIG. 12, the controller 400 is a tablet terminal, and includes a display 410 and a touch panel input 420. The input 420 can be used by the user to input the selection information 40.

The controller 400 acquires the captured microscope images (the first image 21 and the second image 22) from the cell imager 200 and displays them on the display 410. The controller 400 receives a user's input operation via the input 420 on the displayed image. The controller 400 transmits the acquired microscope images (the first image 21 and the second image 22) to the cell image analyzer 100, and transmits the selection information 40 received from the user via the input 420 to the cell image analyzer 100. The controller 400 controls the picking operation of the cell picking device 300 by transmitting coordinate information to the cell picking device 300. The cell image analyzer 100 may function as the controller 400 without providing the controller 400.

The cell picking device 300 is configured to pick cells in the culture vessel 90 placed on the stage 450. In the example of FIG. 12, the cell picking device 300 includes a nozzle 310, a suction mechanism 320, and a nozzle movement mechanism 330.

The nozzle 310 is configured to access the inside of the culture vessel 90 and suction cells. A disposable pipette tip 340 of the nozzle 310 is attachable and detachable, for example. The nozzle 310 suctions cells from the tip end of the attached pipette tip 340. The suction mechanism 320 is fluidly connected to the nozzle 310 and applies a suction force to the nozzle 310. The nozzle movement mechanism 330 is configured to move the nozzle 310. The nozzle movement mechanism 330 is a robot mechanism including a drive source such as a motor, moves the tip end of the nozzle 310 to picking coordinates in the culture vessel 90 at the time of picking, and retracts the tip end of the nozzle 310 to the outside of the culture vessel 90 after suction. The cell picking device 300 is controlled by the controller 400 to start and end the picking operation, and receives an input of the picking coordinates from the controller 400.

The stage 450 is an electric stage, for example. In this case, the controller 400 can control the stage 450 such that microscope images of a predetermined range in the culture vessel 90 are sequentially acquired. The stage 450 may not be an electric stage. In this case, in the picking operation, the user can grasp and move the culture vessel 90 on the stage 450, for example, to sequentially acquire a plurality of microscope images at imaging positions in the culture vessel 90.

In an example of FIG. 11, the processor 120 of the cell image analyzer 100 includes the segmentation processing unit 121, the determination processing unit 122, and a picking processing unit 123 as functional blocks. The segmentation processing unit 121 performs the segmentation process on the microscope images (the first image 21 and the second image 22) using the second trained model 60 stored in the storage 110. The determination processing unit 122 acquires the second image 22 and the selection information 40 via the controller 400, creates the first trained model 50, and stores it in the storage 110. The determination processing unit 122 performs the determination process on the cell colony 10 in the first image 21 using the first trained model 50 stored in the storage 110. The picking processing unit 123 determines whether or not the cell colony 10 corresponds to the picking target, and sets picking coordinates 26 (see FIG. 8) for the cell colony 10 corresponding to the picking target.

The storage 110 stores the second trained model 60 in advance. The segmentation process does not depend on the user's preference (the tendency of which cell colony 10 is determined as the picking target), and thus the second trained model 60 created by performing machine learning in advance can be stored. Image data including the first image 21 and the second image 22 and the selection information 40, for example, are input to and stored in the storage 110.

In the cell image analyzer 100, the creation process for the first trained model 50 shown in FIG. 5 is performed as a preparatory work before the first image 21 is acquired and the determination process and a picking process are performed. That is, the first trained model 50 is created in advance by the second image 22 as a sample, and is stored in the storage 110.

First, the user prepares the culture vessel 90 containing a sample cultured cell and places it on the stage 450. The second image 22 is captured by the cell imager 200 and transmitted to the cell image analyzer 100 via the controller 400 (step 81 of FIG. 5).

The segmentation processing unit 121 performs the segmentation process by the second trained model 60 to generate the label image 22A of the second image 22 (step 82 of FIG. 5). As shown in FIG. 6, the controller 400 displays the second image 22 or the generated label image 22A on the display 410, and receives the input of the selection information 40 from the user via the input 420 (step 83 of FIG. 5). The image display and input reception can also be performed using the display 130 and the input 140 (see FIG. 11) of the cell image analyzer 100.

When inputting the selection information 40, the user taps the image of the cell colony 10 on a screen when the cell colony 10 including a desired colony region is present in the displayed image, as shown in FIG. 6, to input the selection information 40 that is a positive example. When the next image is displayed without tapping the image, the selection information 40 that is a negative example is attached to the cell colony 10. The controller 400 transmits the selection information 40 to the cell imager 200.

When the selection information 40 is acquired, the determination processing unit 122 calculates the shape feature amounts 25 of the cell colony 10 from the label image 22A (step 84 of FIG. 5). The determination processing unit 122 calculates one or a plurality of shape feature amounts 25 set in advance among the various shape feature amounts shown in FIG. 7.

The determination processing unit 122 performs machine learning using the shape feature amounts 25 of the cell colony 10 and the selection information 40 regarding the cell colony 10 (step 85 of FIG. 5). The user repeats the above operations to perform machine learning a predetermined number of times required to create the first trained model 50 (step 86 of FIG. 5). Thus, the creation of the first trained model 50 as the preparatory work is completed. The created first trained model 50 is stored in the storage 110 (step 87 of FIG. 5).

In the creation process for the first trained model 50, the picking operation may be actually performed. That is, when the user taps the cell colony 10 in the displayed image, the controller 400 acquires the tapped position as the picking coordinates 26 (see FIG. 6). The controller 400 transmits the acquired picking coordinates 26 and a picking operation start command to the cell picking device 300. Thus, the cell picking device 300 picks the colony region 11 at the specified picking coordinates.

According to this configuration, the user can perform the creation process (machine learning) for the first trained model 50, which is the preparatory work, simply by actually performing the picking operation such as passaging by manual input. For example, when there are a plurality of culture vessels 90 on which the picking operation should be performed, the user causes the cell picking system 500 to perform the picking operation on the first culture vessel 90 by manual input. A large number of cell colonies 10 to be determined are contained in the culture vessel 90, and thus when the picking operation on the first culture vessel 90 is completed, for example, the creation process for the first trained model 50 by machine learning is also completed. The picking operation on the second and subsequent culture vessels 90 can be automatically or semi-automatically performed using the created first trained model 50, as described below.

Image Analysis Process and Picking Process

An image analysis process and the picking process by the cell picking system 500 using the first trained model 50 created in advance are now described with reference to FIG. 13.

Step 151 of FIG. 13 corresponds to step 71 of the cell image analysis method according to this embodiment shown in FIG. 2. Step 152 of FIG. 13 corresponds to step 72 shown in FIG. 2. Step 153 of FIG. 13 corresponds to step 73 shown in FIG. 2. Step 154 of FIG. 13 corresponds to step 76 shown in FIG. 2. In an example of FIG. 13, the cell image analysis method includes step 71 to step 76 of FIG. 2, and acquires the determination result 35 as to whether or not the cell colony 10 includes the colony region that is a candidate for a search target. The cell image analysis method includes step 156 of setting the picking coordinates 26 of the colony region 11 determined to be desired by the user based on the determination result 35 as to whether or not the cell colony 10 includes the colony region that is a candidate for a search target, and step 157 of picking cells at the picking coordinates 26 from the culture vessel 90.

In step 151, the cell imager 200 images the cell colony 10 in the culture vessel 90 on the stage 450 and generates the first image 21 showing the cell colony 10 included in the imaging field of view. The segmentation processing unit 121 of the cell image analyzer 100 acquires the first image 21 via the controller 400.

In step 152, the segmentation processing unit 121 performs the segmentation process on the acquired first image 21. That is, the segmentation processing unit 121 generates the label image 21A of the first image 21 by inputting the first image 21 to the second trained model 60.

In step 153, the determination processing unit 122 acquires the shape feature amounts 25 of the cell colony 10 from the generated label image 21A. That is, the determination processing unit 122 calculates one or a plurality of shape feature amounts 25 set in advance among the examples shown in FIG. 7.

In step 154, the determination processing unit 122 determines whether or not each cell colony 10 includes the colony region that is a candidate for a search target. That is, the determination processing unit 122 inputs the shape feature amounts 25 of each cell colony 10 to the first trained model 50 to output the determination result 35 as to whether or not each cell colony 10 is a positive example (includes the colony region that is a candidate for a search target). The determination result 35 is output as a certainty (numerical value) from 0(%) to 100(%).

In step 155, the picking processing unit 123 of the cell image analyzer 100 determines whether or not the cell colony 10 for which the determination result 35 has been output corresponds to the picking target. When determining that the cell colony 10 for which the determination result 35 has been output does not correspond to the picking target, the picking processing unit 123 advances to step 158.

When determining that the cell colony 10 for which the determination result 35 has been output corresponds to the picking target, the picking processing unit 123 sets the picking coordinates 26 of the colony region 11 determined to be desired by the user in step 156.

In an example of passaging, position coordinates in the colony region 11 of undifferentiated cells of the cell colony 10 determined to correspond to the picking target are set to the picking coordinates 26. For example, as illustrated in FIG. 8, the picking processing unit 123 calculates the geometric center of gravity in the colony region 11 of undifferentiated cells, and sets a position of the calculated center of gravity at the picking coordinates 26. Furthermore, the picking processing unit 123 acquires the contour shape of the region actually picked by the cell picking device 300 in advance, and sets the picking coordinates 26 as a position at which the picked region fits within the colony region 11 of undifferentiated cells. The picking processing unit 123 outputs the set picking coordinates 26 to the controller 400.

In step 157, the cell picking device 300 picks cells at the picking coordinates 26 from the culture vessel 90 under the control of the controller 400. The cell picking device 300 extracts the cells (colony region) at the picking coordinates 26 into the pipette tip by moving the tip end of the nozzle 310 at the picking coordinates 26 transmitted from the controller 400 and suctioning the cells. The cell picking device 300 retracts the tip end of the nozzle 310 to the outside of the culture vessel 90, and then discharges the extracted cells to a cell container at a predetermined position. When the picking is completed, the process advances to step 158.

In step 158, the controller 400 determines whether or not the picking operation is terminated. When determining that the picking operation is not terminated, the controller 400 returns the process to step 151 to acquire the next first image 21. The controller 400 determines that the picking operation is terminated when an operation input is received from the user to terminate the picking operation, when a predetermined number of cell colonies 10 are picked, or when the above process is performed on all cell colonies 10, for example.

This completes the image analysis process and the picking process using the first trained model 50.

FIG. 13 shows an example in which the determination process is performed each time the first image 21 is acquired at each imaging position in the culture vessel 90 (hereinafter referred to as a sequential process). In this embodiment, unlike this, a plurality of first images 21 may be captured in advance at imaging positions in the culture vessel 90, and the determination process may be collectively performed on cell colonies 10 appearing in each of the captured first images 21 (hereinafter referred to as a batch process). In the case of the batch process, after the determination result 35 of each cell colony 10 imaged in advance is obtained, it is determined whether or not each cell colony 10 is to be picked based on each determination result 35.

Figure 14:
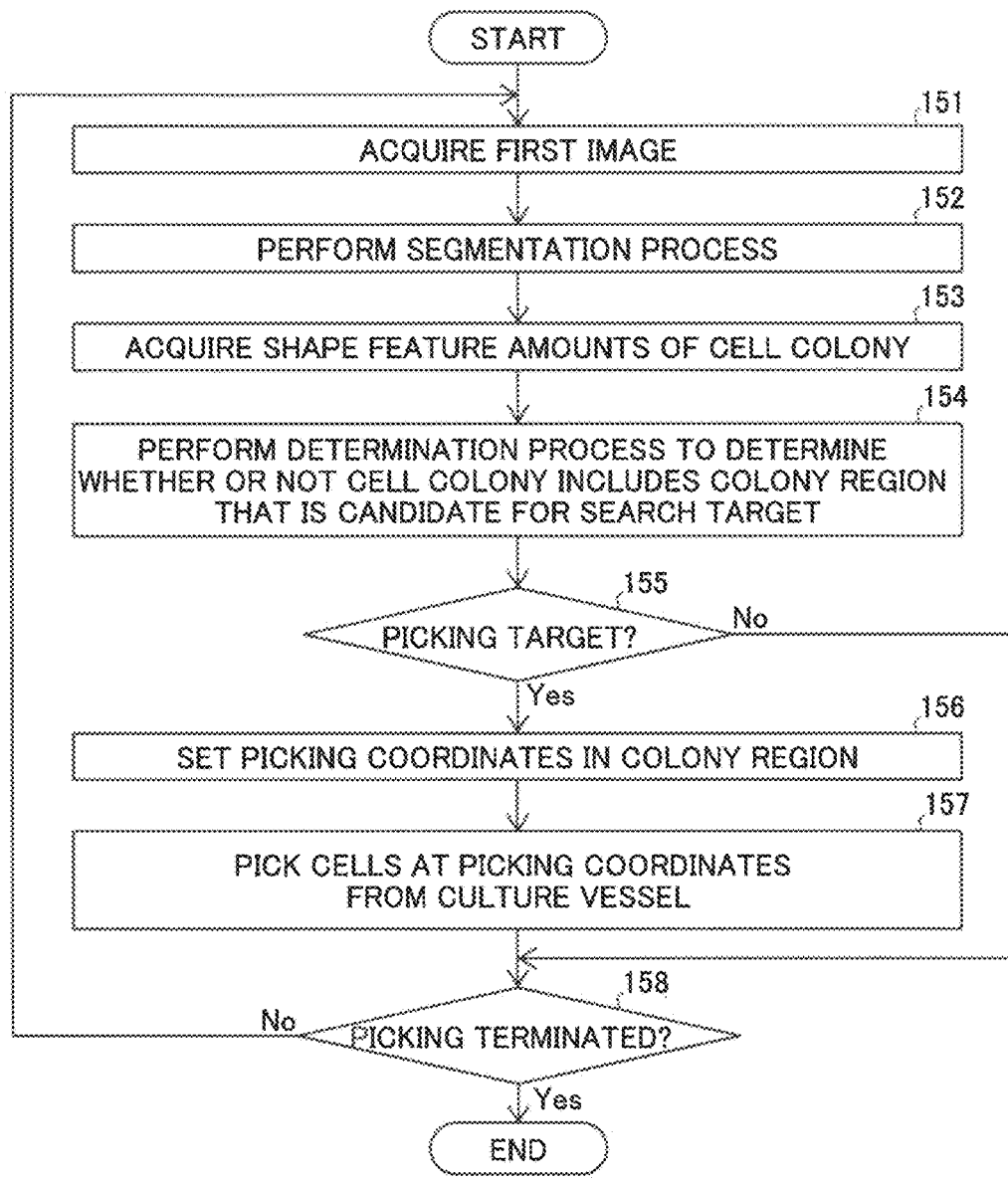
FIG. 14 is a diagram showing examples of determination criteria for a picking target.

FIG. 14 shows examples of criteria for determining whether or not the cell colony 10 corresponds to the picking target in step 155. When the value (certainty) of the determination result 35 is larger than a preset threshold, for example, as a first determination criterion, the picking processing unit 123 determines that the cell colony 10 corresponds to the picking target. The threshold is input in advance by the user. The user sets a relatively high threshold when he/she wants to carefully select the cell colony 10 to be picked, and sets a relatively low threshold when he/she wants to pick as many cell colonies 10 as possible. The first determination criterion can be applied to both the sequential process and the batch process.

When the ranks of the values (certainties) of the determination results 35 of a plurality of cell colonies 10 are higher than a preset rank threshold, as a second determination criterion, the picking processing unit 123 determines that the cell colony 10 corresponds to the picking target. The second determination criterion can be applied to the batch process. That is, after the determination process is first performed on the plurality of (all) cell colonies 10 appearing in the plurality of first images 21 by the batch process, each cell colony 10 is ranked according to the determination result 35, and the top N cell colonies 10 having a high value of the determination result 35 are set as picking targets. The rank threshold N is input in advance by the user.

The picking process can be performed fully automatically by presetting the thresholds for the first determination criterion and the second determination criterion. In addition, when an input operation indicating that the cell colony 10 is to be picked is received, as a third determination criterion, the picking processing unit 123 determines that the cell colony 10 corresponds to the picking target. For example, the value (certainty) of the determination result 35 is displayed on the display 410 together with an image of the cell colony 10, and the user is caused to input whether or not the displayed cell colony 10 is selected as the picking target via the input 420. The user can determine whether or not the cell colony 10 is set as the picking target after confirming the cell colony 10 by himself/herself with reference to the numerical value of the determination result 35.

Advantages of this Embodiment

In this embodiment, the following advantages are obtained.

As described above, the cell image analysis method according to this embodiment includes step 71 of acquiring the first image 21 of the cell colony 10 including the cells having differentiation potential, step 72 of converting the first image 21 into the label image 21A by performing the segmentation process to identify the colony region 12 of cells (undifferentiated deviant cells) that have already started differentiation and the colony region 11 of undifferentiated cells in the cell colony 10 in the first image 21, step 73 of acquiring the shape feature amounts 25 of the cell colony 10 from the label image 21A, step 74 of receiving the input regarding the colony region of a search target from the user using a computer, step 75 of setting the determination criteria 30 for the shape feature amounts 25 based on the user's input, and step 76 of determining whether or not each cell colony 10 includes the colony region that is a candidate for a search target based on the shape feature amounts 25 and the determination criteria 30.

As described above, the cell image analyzer 100 according to this embodiment includes the storage 110 configured to allow the microscope image (first image 21) of the cell colony 10 including the cells having differentiation potential to be input thereto, the segmentation processing unit 121 configured to convert the microscope image (first image 21) into the label image 21A by performing the segmentation process to identify the colony region 12 of cells that have already started differentiation and the colony region 11 of undifferentiated cells in the cell colony 10 in the microscope image, the input 140 configured to receive the input regarding the colony region of a search target, and the determination processing unit 122 configured to determine whether or not each cell colony 10 included in the microscope image includes the colony region that is a candidate for a search target, and the determination processing unit 122 is configured to acquire the shape feature amounts 25 of the cell colony 10 from the label image 21A and determine the colony region based on the shape feature amounts 25 and the determination criteria 30 for the shape feature amounts 25 set based on the user's input.

According to the above configuration, among the colony region 12 of cells that have started differentiation and the colony region 11 of undifferentiated cells, the colony region that may be the picking target according to the purpose of culture, for example, can be identified from the image by the segmentation process. Furthermore, the determination result 35 as to whether or not each cell colony 10 in the image includes the colony region that is a candidate for a search target can be obtained based on the shape feature amounts 25 and the determination criteria 30 for the shape feature amounts 25 set based on the user's input. Consequently, in this embodiment, the cell colony 10 including the colony region that is likely to be determined by the user as the picking target can be determined and shown to the user, and thus it is no longer necessary for the user to observe and determine a large number of cell regions in the microscope image one by one. Thus, the load on the user associated with the search operation for cells to be picked in cell culture can be effectively reduced.

In the example of the above embodiment, with the following configurations, further advantages are obtained.

That is, the cell image analysis method according to the above embodiment includes step 83 of receiving the input of the selection information 40 as to whether or not the cell colony 10 in the second image 22 acquired in advance includes a desired colony region from the user and step 85 of setting the determination criteria 30 based on the received selection information 40. With this configuration, the user inputs the user's own determination result for the cell colony 10 in the second image 22 as a sample such that the determination criteria 30 as to whether or not the cell colony 10 includes the "colony region that is a candidate for a search target" can be set. In this case, it is not necessary for the user to find optimum values for the thresholds of the shape feature amounts 25 and the weights of the plurality of shape feature amounts 25, for example, which are the determination criteria 30, and thus the workload on the user for setting the determination criteria 30 can be reduced.

In the cell image analysis method according to the above embodiment, step 75 of setting the determination criteria 30 includes creating the first trained model 50 that has acquired the determination criteria 30 for the shape feature amounts 25 by machine learning using the shape feature amounts 25 acquired from the label image 22A of the second image 22 as input data and the selection information 40 as teaching data. Furthermore, step 76 of determining whether or not the cell colony 10 includes the colony region that is a candidate for a search target includes inputting the shape feature amounts 25 acquired from the label image 21A of the first image 21 to the first trained model 50 to generate the determination result 35. With this configuration, the user can obtain the first trained model 50 that has acquired the determination criteria 30 for the shape feature amounts 25 by machine learning simply by inputting the selection information 40. Consequently, the determination result 35 generated by the first trained model 50 can be provided to the user. The colony region appearing in the first image 21 has various morphologies, and the user's preference (the tendency of selection of the picking target) is also various. Therefore, in practice, it is difficult to construct the determination criteria 30 to generate the determination result 35 according to the user's preference by a rule-based method that does not rely on machine learning. On the other hand, when a machine learning method is used, even construction of the determination criteria 30 for a plurality of combined shape feature amounts 25 can be easily performed as compared with the rule-based method. By learning using the selection information 40, which is the result of the user's own determination, it is possible to easily provide the determination result 35 with high accuracy according to the user's preference.

In the cell image analysis method according to the above embodiment, step 83 of receiving the input of the selection information 40 includes allowing the user to specify the colony region in the second image 22 or the label image 22A of the second image 22 or allowing the user to pick the colony region. With this configuration, the user can input the selection information 40 as a sample for setting the determination criteria 30 simply by specifying the colony region to determine the picking target for the cell picking device 300. Therefore, it is not necessary to perform a special input operation to input the selection information 40, and thus the workload on the user for setting the determination criteria 30 can be reduced.

In the cell image analysis method according to the above embodiment, the shape feature amounts 25 include the shape feature amount related to at least one of i) the entire region of the cell colony 10 included in the label image 21A, ii) the colony region 11 of undifferentiated cells included in the cell colony 10, or iii) the colony region 12 of undifferentiated deviant cells that have started differentiation included in the cell colony 10. As a result of earnest studies, the inventor has found that even when the user himself/herself determines the picking target from the microscope image, the overall shape of the cell colony 10, the shape of the colony region 11 of undifferentiated cells, and the shape of the colony region 12 of undifferentiated deviant cells greatly influence determination of the user. Therefore, such a shape feature amount 25 is used such that it is possible to easily and accurately determine whether or not the cell colony 10 includes the colony region that is a candidate for a search target.

In the cell image analysis method according to the above embodiment, the shape feature amounts 25 include at least one of i) the area of the region, ii) the contour length of the region, iii) the degree of circularity of the region, iv) the aspect ratio of the minimum circumscribed rectangle of the region, or v) the area ratio of the colony region 11 to the entire region of the cell colony 10. With this configuration, it is possible to obtain a useful feature amount that characterizes the entire cell colony 10 or the colony region in order to determine whether or not the cell colony 10 includes the colony region that is a candidate for a search target.

In the cell image analysis method according to the above embodiment, step 72 of converting the first image 21 into the label image 21A includes generating the label image 21A by the second trained model 60 configured to assign the segmentation result labels to the colony regions (11 and 12), using the microscope image (input image 23) of the cell colony 10 as input data. With this configuration, a highly accurate segmentation process can be performed by the second trained model 60 that has learned the morphologies of the various cell colonies 10. As described above, the colony region 11 appearing in the microscope image has various morphologies, and it is difficult to achieve a segmentation process that can accurately identify the colony region 11 (an undifferentiated region and a deviant region) having various morphologies by a rule-based method that does not rely on machine learning. On the other hand, when a machine learning method is used, it is possible to cause a training model to learn even morphological features that are hardly defined by a rule, and it is possible to achieve a highly accurate segmentation process.

The cell image analysis method according to the above embodiment further includes step 156 of setting the picking coordinates 26 of the colony region 11 determined to be desired by the user based on the determination result 35 as to whether or not the cell colony 10 includes the colony region that is a candidate for a search target obtained in step 71 to step 76, and step 157 of picking the cells at the picking coordinates 26 from the culture vessel 90. With this configuration, it is possible to perform an automatic picking operation on the colony region determined to be the picking target based on the determination result 35 as well as providing the user with the determination result 35 as to whether or not the cell colony 10 includes the colony region that is a candidate for a search target. Consequently, that is, not only the picking target search operation but also the picking operation after the search can be automated or semi-automated, and thus the workload on the user in the entire picking operation related to cell culture can be effectively reduced.

Modified Example

A modified example of the cell image analysis method is now described with reference to FIGS. 15 and 16.

Figure 15:
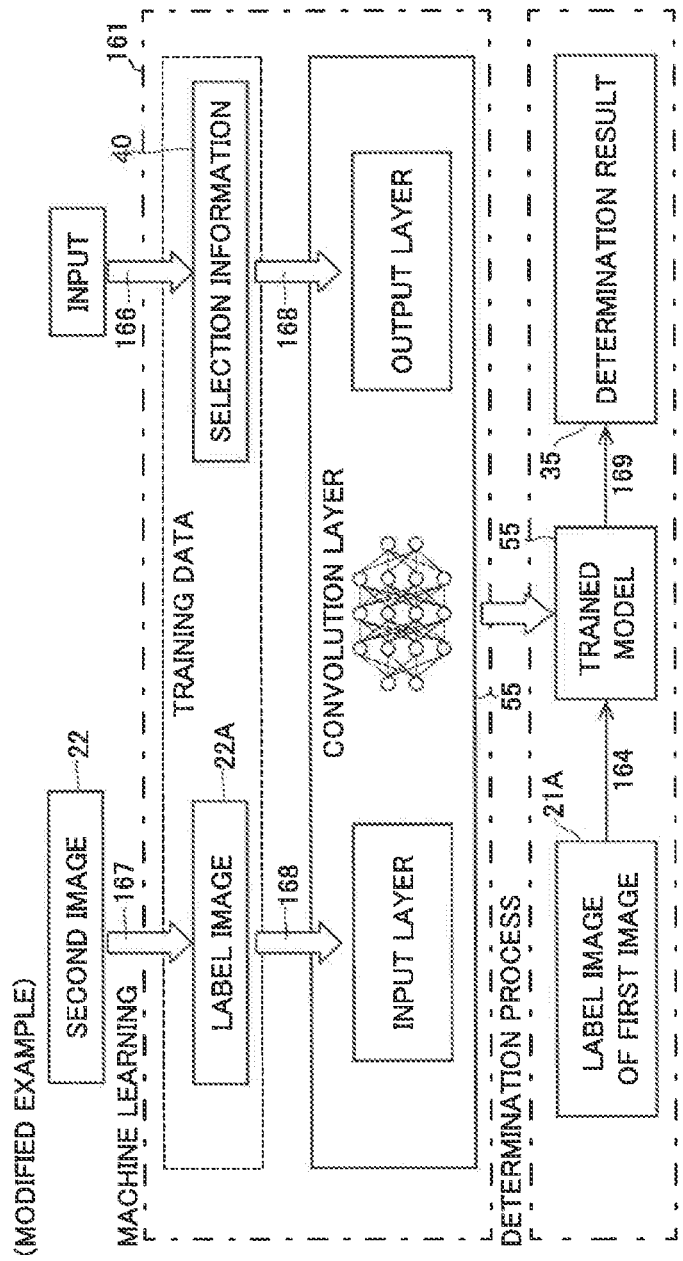
FIG. 15 is a diagram illustrating a trained model for determination according to a modified example.
Figure 16:
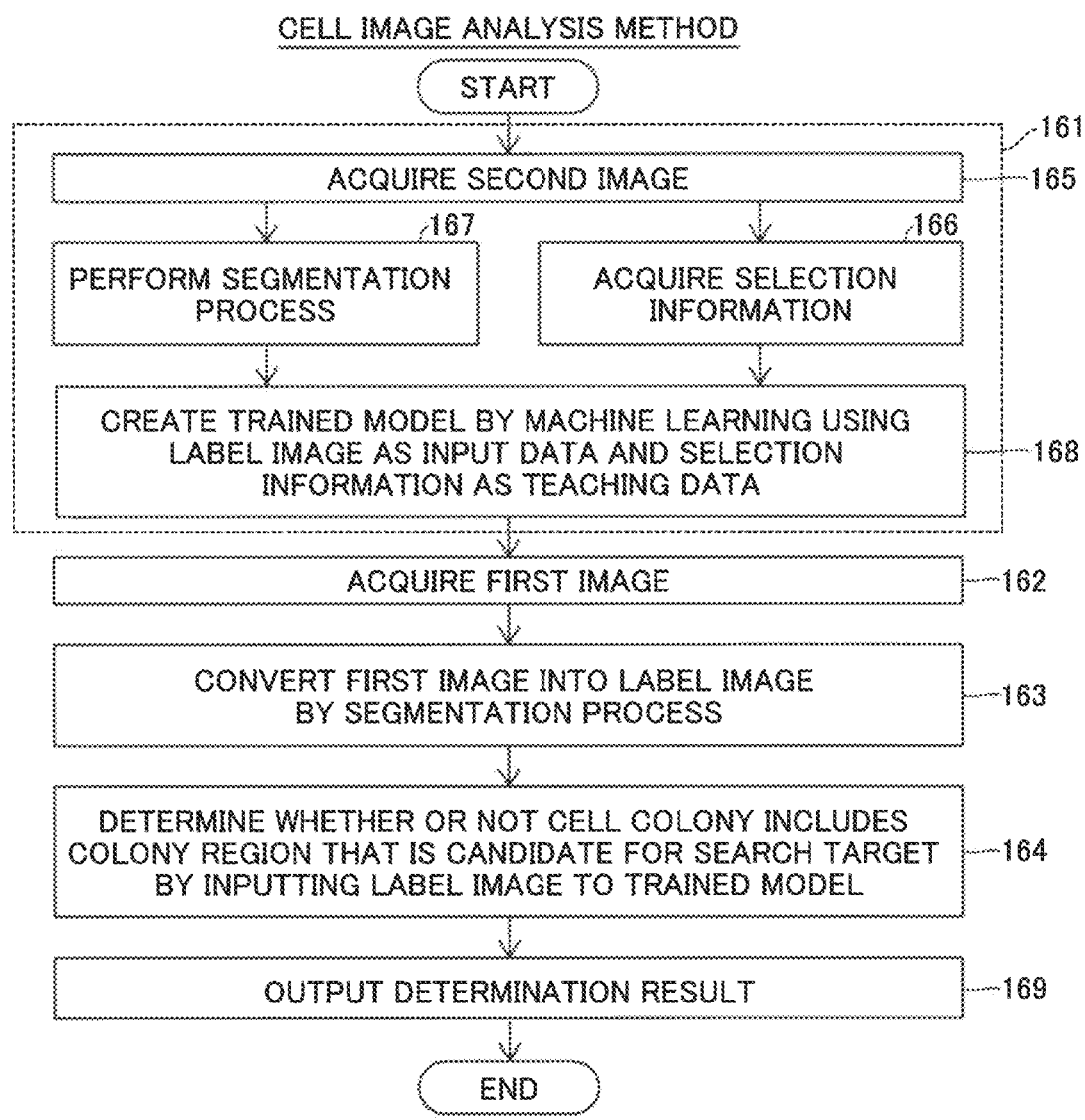
FIG. 16 is a flowchart illustrating a cell image analysis method according to the modified example.

While the example in which the shape feature amounts 25 of the cell colony 10 are acquired from the segmented label image 21A, and the determination process is performed based on the shape feature amounts 25 has been shown in the aforementioned embodiment, in the modified example shown in FIGS. 15 and 16, a determination process is performed without using shape feature amounts 25 of a cell colony 10. A cell image analysis method according to the modified example can be executed with the same hardware configuration as that of the above embodiment, and thus description of the hardware is omitted.

The cell image analysis method according to this modified example includes step 161 of creating a machine-trained model 55 for determination, step 162 of acquiring a first image 21 of a cell colony 10 including cells having differentiation potential, step 163 of converting the first image 21 into a label image 21A by performing a segmentation process to identify a colony region 12 of cells that have already started differentiation and a colony region 11 of undifferentiated cells in the cell colony 10 in the first image 21, and step 164 of determining whether or not each cell colony 10 includes a colony region that is a candidate for a search target by inputting the label image 21A of the first image 21 to the trained model 55.

Step 161 of creating the trained model 55 for determination includes step 166 of receiving an input of selection information 40 as to whether or not the cell colony 10 in a second image 22 acquired in advance includes a desired colony region and step 168 of creating the trained model 55 by machine learning using a label image 22A obtained by segmenting the second image 22 as input data and the selection information 40 as teaching data.

Thus, the second image 22 is used as a sample to create the trained model 55 for determination. First, in step 165, the second image 22 is acquired. In step 166, the input of the selection information 40 is received. In step 167, the segmentation process is performed on the second image 22. Step 165 to step 167 are similar to step 81 to step 83 of FIG. 5.

In the modified example, shape feature amounts 25 are not calculated unlike the example of FIG. 5. In the modified example, as shown in FIG. 15, the label image 22A of the second image 22 is used as input data instead of the shape feature amounts 25. The selection information 40 is used as teaching data. Therefore, in step 168, a training model learns to determine (guess) whether or not the cell colony 10 is a positive example (includes the colony region that is a candidate for a search target) when the label image 21A of the cell colony 10 of interest is given by machine learning using the label image 21A as input data and the selection information 40 as teaching data.

As a machine learning method, any method such as a convolutional neural network, a neural network, an SVM, or boosting can be used. From the viewpoint of the identification performance of a label region, it is preferable to use a convolutional neural network for the trained model 55 for determination according to the modified example.

When the training model tries to determine whether or not the cell colony 10 includes the colony region that is a candidate for a search target from a cell image, information contained in the image may be too diverse and a determination result 35 may hardly converge. However, when the label image 22A by the segmentation process is used as an input image as in this modified example, the input image is segmented by label regions of three classes (at least two classes), and information on variations in brightness in the image due to a cell surface texture (pattern), illumination light, or extraneous light, for example, is removed. That is, it can be said that the label image 22A is obtained by selectively extracting only information on the shape of the cell colony 10. Consequently, in machine learning using the label image 22A as an input image, it is possible to effectively learn to determine whether or not the cell colony 10 is a positive example based on the shape of the cell colony 10 in the image, similarly to the shape feature amounts 25 in the above embodiment.

When the trained model 55 for determination is created by machine learning using the second image 22, preparations for cell image analysis for the first image 21 are completed.

As shown in FIG. 16, in the cell image analysis using the trained model 55, first, the first image 21 is acquired in step 162, and the label image 21A of the first image 21 is generated by the segmentation process on the first image 21 in step 163. Step 162 and step 163 are similar to step 71 and step 72 shown in FIG. 2.

In step 164, the determination result 35 as to whether or not each cell colony 10 includes the colony region that is a candidate for a search target is generated by inputting the generated label image 21A of the first image 21 to the trained model 55 for determination. In step 169, the generated determination result 35 is output.

Advantage of Cell Image Analysis Method According to Modified Example

According to this modified example, among the colony region 12 of cells that have started differentiation and the colony region 11 of undifferentiated cells, a colony region that may be a picking target according to the purpose of culture, for example, can be identified from the image by the segmentation process. Furthermore, the determination result 35 as to whether or not each cell colony 10 in the image includes the colony region that is a candidate for a search target can be obtained by the trained model 55 machine-trained using the selection information 40 as to whether or not the cell colony 10 includes the desired colony region. Consequently, according to the modified example, the cell colony 10 including the colony region that is likely to be determined by a user as the picking target can be determined and shown to the user, and thus it is no longer necessary for the user to observe and determine a large number of cell regions in a microscope image one by one. Thus, the load on the user associated with a search operation for cells to be picked in cell culture can be effectively reduced.

Other Modified Examples

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the example in which the cell colony 10 including the colony region 11 of undifferentiated cells is determined as the picking target for the picking operation for passaging in cell culture has been shown in the aforementioned embodiment, the present invention is not limited to this. As described above, the cell colony 10 including the colony region 12 of undifferentiated deviant cells may be determined as the picking target. That is, the determination process may be performed assuming that the colony region 12 of undifferentiated deviant cells is the colony region that is a candidate for a search target. The determination criteria 30 are different between the colony region 11 of undifferentiated cells and the colony region 12 of undifferentiated deviant cells, and thus the determination criteria 30 are set separately according to the purpose of picking. The selection information 40 input as teaching data in a case of the colony region 12 of undifferentiated deviant cells is different from that in a case of the colony region 11 of undifferentiated cells, and thus the first trained model 50 (trained model 55 for determination) is created separately. The storage 110 shown in FIG. 3 may separately store a first trained model 50 for passaging and a first trained model 50 for removing undifferentiated deviant cells, and switch the trained model used according to the user's purpose.

While the example in which the segmentation process of three classes of undifferentiated cells, undifferentiated deviant cells, and a background is performed has been shown in the aforementioned embodiment, the present invention is not limited to this. In the present invention, a segmentation process may be further performed to perform two-class classification into live cells and dead cells, for example. Alternatively, a segmentation process may be further performed to perform two-class classification into cells attached to a well and detached cells. According to this, for example, the cell colony 10 including the colony region that is a candidate for a search target can be determined from among cell colonies 10 including colony regions of "live cells" and "undifferentiated cells", and the cell colony 10 including the colony region that is a candidate for a search target can be determined from among cell colonies 10 including colony regions of "attached cells" and "undifferentiated cells". As yet another example, a class of "foreign matter" other than cells may be added, and the foreign matter mixed in the culture vessel 90 may be found and removed.

While the example in which the cell image analyzer 100 is communicably connected to the cell imager 200 has been shown in the aforementioned embodiment, the present invention is not limited to this. In the present invention, a portion or all of the process performed by the cell image analyzer 100 may be performed via a network.

Figure 17:
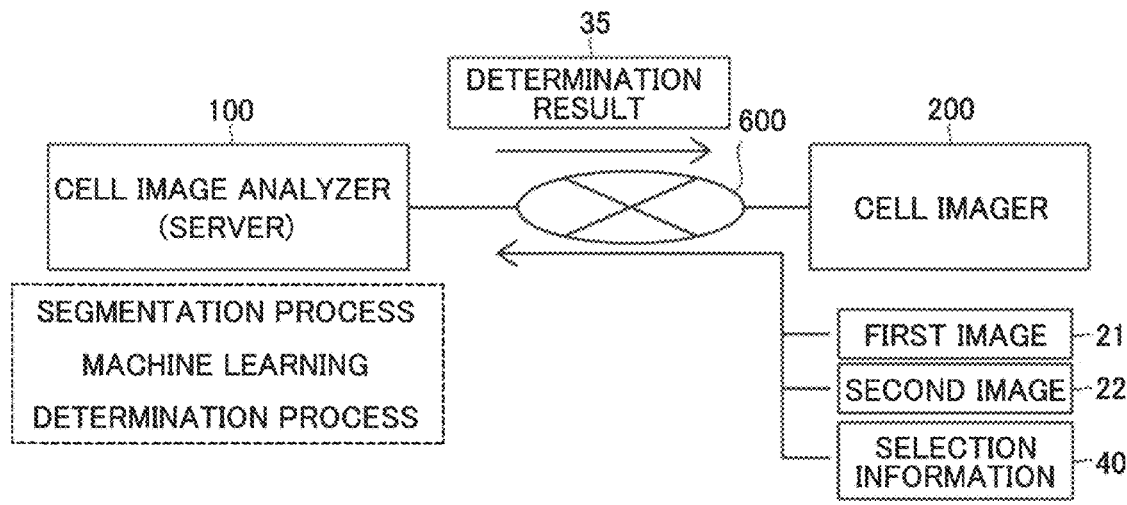
FIG. 17 is a schematic view showing a modified example in which a segmentation process and a determination process are performed on the server side.

For example, in a modified example shown in FIG. 17, a cell image analyzer 100 at a remote location is configured as a server device connected to a cell imager 200 via a network 600. A user uses the cell imager 200 to image a first image 21 and a second image 22, and inputs selection information 40. The cell imager 200 transmits the first image 21, the second image 22, and the selection information 40 to the cell image analyzer 100 via the network 600. The cell image analyzer 100 performs a segmentation process to generate label images 21A and 22A. The cell image analyzer 100 creates a first trained model 50 using the generated label image 22A and the received selection information 40. The cell image analyzer 100 inputs the label image 21A of the first image 21 to the first trained model 50, performs a determination process, and transmits a determination result 35 to the cell imager 200. Thus, the user can acquire the determination result 35 for each cell colony 10 included in the first image 21 and perform a picking operation using the determination result 35.

While the example in which the cell image analyzer 100 performs the segmentation process, creates the first trained model 50, and performs the determination process has been shown in the aforementioned embodiment, the present invention is not limited to this. In the present invention, a portion of the process performed by the cell image analyzer 100 may be performed by another device.

Figure 18:
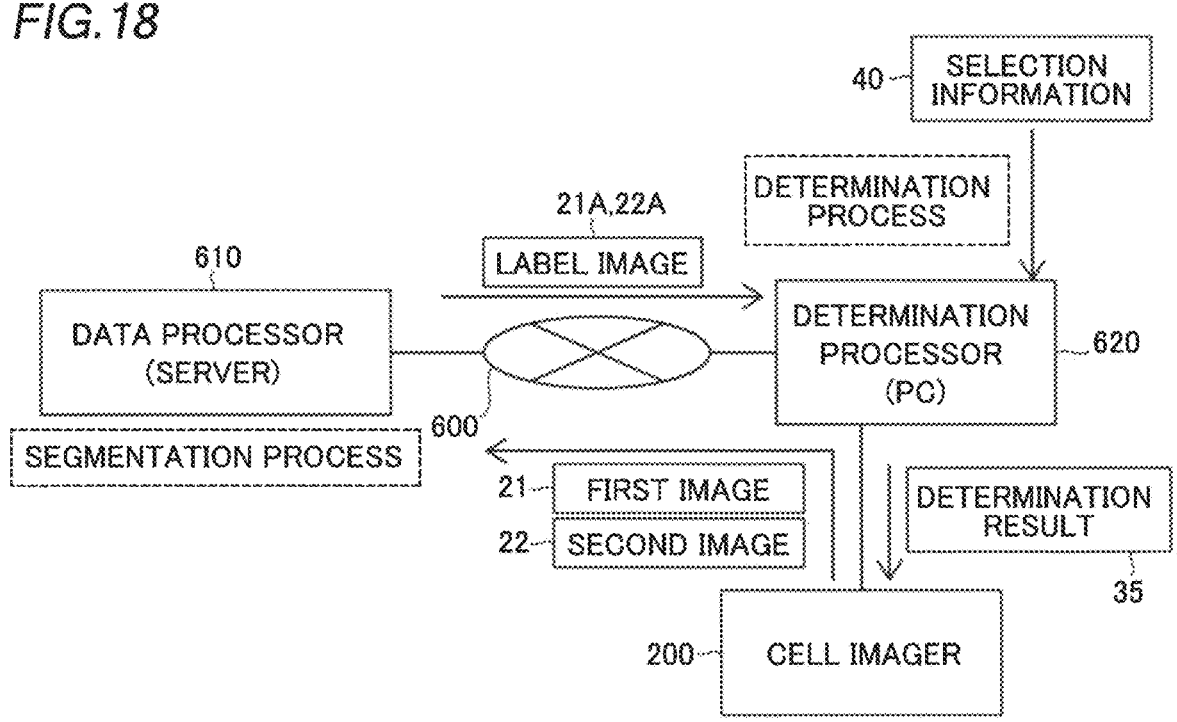
FIG. 18 is a schematic view showing a modified example in which a segmentation process is performed on the server side.

For example, in a modified example shown in FIG. 18, a data processor 610, which is a server device at a remote location, is communicably connected to a determination processor 620 via a network 600. A data processor 610 receives a microscope image (a first image 21 or second image 22) from the determination processor 620, which is a PC used by a user, and performs a segmentation process. The data processor 610 performs the segmentation process using a second trained model 60, for example, and transmits a generated label image (21A or 22A) to the determination processor 620. The determination processor 620 creates a first trained model 50 by machine learning using the label image 22A of the second image 22 received from the data processor 610 and selection information 40 received from the user. The determination processor 620 calculates shape feature amounts 25 of a cell colony 10 from the label image 21A of the first image 21 received from the data processor 610, and performs a determination process using the first trained model 50. The determination processor 620 acquires a determination result 35 by inputting the shape feature amounts 25 to the first trained model 50. The user can acquire the determination result 35 for each cell colony 10 included in the first image 21 and perform a picking operation using the determination result 35.

Thus, the cell image analysis method according to the present invention may be executed in the form of a so-called cloud service, for example, by cooperation of a plurality of computers connected to the network.

While the example in which the area, the contour length, the degree of circularity, and the aspect ratio of the region of interest, the area ratio to the entire region of the cell colony, etc. are used as the shape feature amounts 25 has been shown in the aforementioned embodiment, the present invention is not limited to this. In the present invention, an amount other than the above may be used as the shape feature amount 25.

While the example in which the determination process is performed using the first trained model 50 has been shown in the aforementioned embodiment, the present invention is not limited to this. As described above, the determination process may be performed using a rule-based method based on the determination criteria 30 such as the thresholds and the weights set according to the user's preference without using the machine learning method.

While the example in which the segmentation process is performed using the second trained model 60 has been shown in the aforementioned embodiment, the present invention is not limited to this. In the present invention, the segmentation process may be performed using a rule-based method using a threshold process or a feature extraction process on an image, for example, without using the machine learning method.

While the example in which the imager 230 of the cell imager 200 is provided in the optical microscope has been shown in FIG. 12, the present invention is not limited to this. In the present invention, the cell imager 200 may be a dedicated device for capturing microscope images of cells, and may not have a function as an optical microscope. In the example shown in FIG. 12, the cell imager 200 functions as an optical microscope, and thus the stage 450 is used as an electric stage. However, the cell imager 200 may include an imager 230 movable with respect to a fixed stage 450.

Aspects

It will be appreciated by those skilled in the art that the exemplary embodiments described above are specific examples of the following aspects.

(Item 1)

A cell image analysis method comprising:
acquiring a first image of a cell colony including a cell having differentiation potential;
converting the first image into a label image by performing a segmentation process to identify a colony region of a cell that has already started differentiation and a colony region of an undifferentiated cell in the cell colony in the first image;
acquiring a shape feature amount of the cell colony from the label image;
receiving an input regarding a colony region of a search target from a user using a computer;
setting a determination criterion for the shape feature amount based on the user's input; and
determining whether or not the cell colony includes a colony region that is a candidate for the search target based on the shape feature amount and the determination criterion.

(Item 2)

The cell image analysis method according to item 1, wherein
the receiving of the input regarding the colony region of the search target includes receiving an input of selection information as to whether or not the cell colony in a second image acquired in advance includes a desired colony region from the user; and
the setting of the determination criterion includes setting the determination criterion based on the received selection information.

(Item 3)

The cell image analysis method according to item 2, wherein
the setting of the determination criterion includes creating a first trained model that has acquired the determination criterion for the shape feature amount by machine learning using the shape feature amount acquired from a label image of the second image as input data and the selection information as teaching data; and
the determining of whether or not the cell colony includes the colony region that is the candidate for the search target includes inputting the shape feature amount acquired from the label image of the first image to the first trained model to generate a determination result.

(Item 4)

The cell image analysis method according to item 2, wherein the receiving of the input of the selection information includes allowing the user to specify the colony region in the second image or a label image of the second image or allowing the user to pick the colony region.

(Item 5)

The cell image analysis method according to item 1, wherein the shape feature amount includes the shape feature amount related to at least one of i) an entire region of the cell colony included in the label image, ii) the colony region of the undifferentiated cell included in the cell colony, or iii) the colony region of the cell that has started differentiation included in the cell colony.

(Item 6)

The cell image analysis method according to item 5, wherein the shape feature amount includes at least one of i) an area of a region, ii) a contour length of the region, iii) a degree of circularity of the region, iv) an aspect ratio of a minimum circumscribed rectangle of the region, or v) an area ratio of the colony region to the entire region of the cell colony.

(Item 7)

The cell image analysis method according to item 1, wherein the converting of the first image into the label image includes generating the label image by a second trained model configured to assign a segmentation result label to the colony region, using a microscope image of the cell colony as input data.

(Item 8)

A cell picking method utilizing the cell image analysis method according to item 1, comprising:
setting picking coordinates of the colony region determined to be desired by the user based on a determination result as to whether or not the cell colony includes the colony region that is the candidate for the search target; and
picking a cell at the picking coordinates from a culture vessel.

(Item 9)

A cell image analyzer comprising:
a storage configured to allow a microscope image of a cell colony including a cell having differentiation potential to be input thereto;
a segmentation processing unit configured to convert the microscope image into a label image by performing a segmentation process to identify a colony region of a cell that has already started differentiation and a colony region of an undifferentiated cell in the cell colony in the microscope image;
an input configured to receive an input regarding a colony region of a search target; and
a determination processing unit configured to determine whether or not the cell colony included in the microscope image includes the colony region that is a candidate for the search target; wherein
the determination processing unit is configured to acquire a shape feature amount of the cell colony from the label image and determine a colony region based on the shape feature amount and a determination criterion for the shape feature amount set based on a user's input.

(Item 10)

A cell image analysis method comprising:
creating a machine-trained model for determination;
acquiring a first image of a cell colony including a cell having differentiation potential;
converting the first image into a label image by performing a segmentation process to identify a colony region of a cell that has already started differentiation and a colony region of an undifferentiated cell in the cell colony in the first image; and
determining whether or not the cell colony includes the colony region that is a candidate for a search target by inputting the label image of the first image to the trained model; wherein
the creating of the trained model includes:

receiving an input of selection information as to whether or not the cell colony in a second image acquired in advance includes a desired colony region; and
creating the trained model by machine learning using a label image obtained by segmenting the second image as input data and the selection information as teaching data.

What is claimed is:

1. A cell image analysis method comprising:
acquiring a first image of a cell colony including a cell having differentiation potential;
converting the first image into a label image by performing a segmentation process to identify a colony region of a cell that has already started differentiation and a colony region of an undifferentiated cell in the cell colony in the first image;
acquiring a numerical value of a shape feature which is a numerical value that expresses a shape of the cell colony in the label image from the label image;
receiving an input regarding a colony region of a search target from a user using a computer;
setting a determination criterion for the numerical value of the shape feature based on the user's input; and
determining whether or not the cell colony includes a colony region that is a candidate for the search target based on the numerical value of the shape feature and the determination criterion,
wherein in the receiving of the input regarding the colony region of the search target, an input is received, from the user, of selection information as to whether or not the cell colony in an image group of the cell colony including cells having differentiation potential includes a desired colony region as a target for picking which is an extraction operation of the cell,
wherein the setting of the determination criterion includes setting the determination criterion based on the received selection information,
wherein the setting of the determination criterion includes creating a first trained model that has acquired the determination criterion for the numerical value of the shape feature by machine learning using the numerical value of the shape feature acquired from the label image of the first image as input data and the selection information as teaching data, and
wherein the determining of whether or not the cell colony includes the colony region that is the candidate for the search target includes inputting the numerical value of the shape feature acquired from the label image of the first image to the first trained model to generate a determination result.

2. The cell image analysis method according to claim 1, wherein the receiving of the input of the selection information includes allowing the user to specify the colony region in the first image or the label image of the first image or allowing the user to pick the colony region.

3. The cell image analysis method according to claim 1, wherein the numerical value of the shape feature includes the numerical value of the shape feature related to at least one of i) an entire region of the cell colony included in the label image, ii) the colony region of the undifferentiated cell included in the cell colony, or iii) the colony region of the cell that has started differentiation included in the cell colony.

4. The cell image analysis method according to claim 3, wherein the numerical value of the shape feature includes at least one of i) an area of a region, ii) a contour length of the region, iii) a degree of circularity of the region, iv) an aspect ratio of a minimum circumscribed rectangle of the region, or v) an area ratio of the colony region to the entire region of the cell colony.

5. The cell image analysis method according to claim 1, wherein the converting of the first image into the label image includes generating the label image by a second trained model configured to assign a segmentation result label to the colony region, using a microscope image of the cell colony as input data.

6. A cell picking method utilizing the cell image analysis method according to claim 1, comprising:
   setting picking coordinates of the colony region determined to be desired by the user based on a determination result as to whether or not the cell colony includes the colony region that is the candidate for the search target; and
   picking a cell at the picking coordinates from a culture vessel.

7. A cell image analyzer comprising:
   a storage configured to allow a microscope image of a cell colony including a cell having differentiation potential to be input thereto;
   a processor configured to convert the microscope image into a label image by performing a segmentation process to identify a colony region of a cell that has already started differentiation and a colony region of an undifferentiated cell in the cell colony in the microscope image; and
   an input configured to receive an input, from a user, regarding a colony region of a search target,
   wherein the processor is further configured to determine whether or not the cell colony included in the microscope image includes the colony region that is a candidate for the search target,
   wherein the processor is further configured to acquire a numerical value of a shape feature which is a numerical value that express a shape of the cell colony in the label image from the label image and determine a colony region based on the numerical value of the shape feature and a determination criterion for the numerical value of the shape feature set based on a user's input,
   wherein the input is configured to receive an input, from the user, of selection information as to whether or not the cell colony in an image group of the cell colony including cells having differentiation potential includes a desired colony region as a target for picking which is an extraction operation of the cell,
   wherein the processor is further configured to set the determination criterion based on the received selection information,
   wherein the processor is further configured to create a first trained model that has acquired the determination criterion for the numerical value of the shape feature by machine learning using the numerical value of the shape feature acquired from the label image of the microscope image as input data and the selection information as teaching data, and
   wherein the processor is further configured to input the numerical value of the shape feature acquired from the label image of the microscope image to the first trained model to generate a determination result, in determining whether or not the cell colony includes the colony region.

8. The cell image analysis method according to claim 1, wherein
   in the step of converting the first image into a label image, the first image is converted into the label image including a label region of the identified region among at least two label regions, the colony region of the undifferentiated cell and the colony region of the cell that has started differentiation,
   in the step of determining whether or not the cell colony includes the colony region that is the candidate for the search target, for each of the cell colonies in the first image whether or not the colony regions that are candidates for the search target are included, based on the numerical values of the shape feature of the label regions obtained from the label image and the determination criterion input by the user by using the computer.

9. The cell image analysis method according to claim 1, wherein
   in the step of converting the first image into a label image, the first image is converted into the label image including a label region of the identified region among at least two label regions, the colony region of the undifferentiated cell and the colony region of the cell that has started differentiation, and
   in the step of determining whether or not the cell colony includes the colony region that is the candidate for the search target, for each of the cell colonies in the first image whether or not the colony regions that are candidates for the search target are included, based on the numerical values of the shape feature of the label regions obtained from the label image and the determination criterion input by the user by using the computer.

* * * * *